United States Patent
Pai et al.

(10) Patent No.: US 9,599,591 B2
(45) Date of Patent: Mar. 21, 2017

(54) LOW COST, PORTABLE SENSOR FOR MOLECULAR ASSAYS

(75) Inventors: Alex H. Pai, Pasadena, CA (US); Stephen A. Chapman, Pasadena, CA (US); Seyed Ali Hajimiri, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 443 days.

(21) Appl. No.: 13/299,087

(22) Filed: Nov. 17, 2011

(65) Prior Publication Data

US 2012/0149129 A1 Jun. 14, 2012

Related U.S. Application Data

(63) Continuation-in-part of application No. 12/762,229, filed on Apr. 16, 2010, now Pat. No. 8,993,236.

(Continued)

(51) Int. Cl.
G01N 27/00 (2006.01)
G01N 27/74 (2006.01)
(Continued)

(52) U.S. Cl.
CPC ....... *G01N 27/745* (2013.01); *G01N 27/3278* (2013.01); *C12Q 1/6825* (2013.01);
(Continued)

(58) Field of Classification Search
CPC ........ C12Q 2563/143; C12Q 2563/149; C12Q 1/6825; C12Q 1/6823; C12Q 1/6834; C12Q 1/6813; C12Q 2525/301; C12Q 2523/303
(Continued)

(56) References Cited

U.S. PATENT DOCUMENTS

| | | |
|---|---|---|
| 3,641,461 A | 2/1972 | Mrozek |
| 3,676,772 A | 7/1972 | Lee |

(Continued)

FOREIGN PATENT DOCUMENTS

| | | |
|---|---|---|
| EP | 1146347 | 10/2001 |
| EP | 2017619 | 1/2009 |

(Continued)

OTHER PUBLICATIONS

Choi J-W et al: "A new magnetic bead-based, filterless bioseparator with planar electromagnet surfaces for integrated biodetection systems", Sensors and Actuators B: Chemical: International Journal Devoted to Research and Development of Physical and Chemical Transducers, Elsevier S. A, Switzerland, vol. 68, No. 1-3, Aug. 25, 2000 (Aug. 25, 2000), pp. 34-39.

(Continued)

*Primary Examiner* — Erik B Crawford
(74) *Attorney, Agent, or Firm* — Knobbe, Martens, Olson & Bear, LLP

(57) ABSTRACT

An integrated sensor that is capable of discriminating the distance of a label from the sensor without using an optical signal. The label is attached to a single probe molecule or a group of probe molecules that interacts with a single or group of target molecules. As a consequence of this interaction, the probe molecule and/or the target molecule undergo a conformal change. This conformal change leads to perturbations in the distance of the label from the sensor. Thus, measurements and properties such as the concentration and the identity of one or more target molecules can be discerned from signals generated by the sensor (or by a plurality of sensors in a sensor array) and subjected to analysis using general purpose programmable computers programmed with suitable software that controls the ana- (Continued)

lytical process, and such measurements and properties can be provided as a result of the analysis.

19 Claims, 8 Drawing Sheets

Related U.S. Application Data

(60) Provisional application No. 61/414,605, filed on Nov. 17, 2010, provisional application No. 61/170,547, filed on Apr. 17, 2009.

(51) Int. Cl.
*G01N 27/327* (2006.01)
*C12Q 1/68* (2006.01)

(52) U.S. Cl.
CPC ..... *C12Q 1/6834* (2013.01); *C12Q 2523/303* (2013.01); *C12Q 2525/301* (2013.01); *C12Q 2563/143* (2013.01)

(58) Field of Classification Search
USPC ........ 73/779; 435/6.1, 6.11, 287.2; 436/526, 436/806; 299/779
See application file for complete search history.

(56) References Cited

U.S. PATENT DOCUMENTS

| | | | |
|---|---|---|---|
| 4,469,863 A | 9/1984 | Ts'o et al. |
| 4,497,998 A | 2/1985 | West |
| 4,719,384 A | 1/1988 | Hauden et al. |
| 4,816,567 A | 3/1989 | Cabilly et al. |
| 4,837,511 A | 6/1989 | Whittington et al. |
| 4,868,525 A | 9/1989 | Dias |
| 4,878,019 A | 10/1989 | Tsaprazis et al. |
| 4,908,112 A | 3/1990 | Pace |
| 4,910,148 A | 3/1990 | Sorensen et al. |
| 4,932,255 A | 6/1990 | Brace et al. |
| 5,001,424 A | 3/1991 | Kellett et al. |
| 5,162,509 A | 11/1992 | Sessler et al. |
| 5,270,163 A | 12/1993 | Gold et al. |
| 5,334,932 A | 8/1994 | Nielsen |
| 5,341,112 A | 8/1994 | Haman |
| 5,354,967 A | 10/1994 | Barzilai et al. |
| 5,369,245 A | 11/1994 | Pickering |
| 5,459,352 A | 10/1995 | Layton et al. |
| 5,512,439 A | 4/1996 | Hornes et al. |
| 5,569,759 A | 10/1996 | Sessler et al. |
| 5,582,981 A | 12/1996 | Toole et al. |
| 5,608,315 A | 3/1997 | Crayton et al. |
| 5,655,665 A | 8/1997 | Allen et al. |
| 5,670,886 A | 9/1997 | Wolff et al. |
| 5,756,291 A | 5/1998 | Griffin et al. |
| 5,818,097 A | 10/1998 | Rohlfing et al. |
| 5,831,331 A | 11/1998 | Lee |
| 5,837,866 A | 11/1998 | Magda et al. |
| 5,851,829 A | 12/1998 | Marasco et al. |
| 5,922,537 A | 7/1999 | Ewart et al. |
| 5,965,371 A | 10/1999 | Marasco et al. |
| 5,969,111 A | 10/1999 | Sessler et al. |
| 5,981,297 A | 11/1999 | Baselt |
| 6,049,157 A | 4/2000 | Kobayashi |
| 6,052,080 A | 4/2000 | Magori |
| 6,078,208 A | 6/2000 | Nolan et al. |
| 6,084,399 A | 7/2000 | Nagaishi et al. |
| 6,090,552 A | 7/2000 | Nazarenko et al. |
| 6,110,660 A | 8/2000 | Kriz et al. |
| 6,127,661 A | 10/2000 | Fry |
| 6,144,068 A | 11/2000 | Kao et al. |
| 6,188,292 B1 | 2/2001 | Liu |
| 6,229,307 B1 | 5/2001 | Umehara et al. |
| 6,303,316 B1 | 10/2001 | Kiel et al. |
| 6,322,963 B1 | 11/2001 | Bauer |
| 6,359,444 B1 | 3/2002 | Grimes |
| 6,377,130 B1 | 4/2002 | Haman |
| 6,387,671 B1 | 5/2002 | Rubinsky et al. |
| 6,482,619 B1 | 11/2002 | Rubinsky et al. |
| 6,489,774 B1 | 12/2002 | van de Goor et al. |
| 6,615,484 B2 | 9/2003 | Kirsten |
| 6,616,824 B1 | 9/2003 | Tanaka |
| 6,638,924 B2 | 10/2003 | Mody et al. |
| 6,705,388 B1 | 3/2004 | Sorgo |
| 6,777,244 B2 | 8/2004 | Pepper et al. |
| 6,819,120 B2 | 11/2004 | Tam |
| 6,900,895 B2 | 5/2005 | Van Wiggeren |
| 6,984,734 B2 | 1/2006 | Sessler et al. |
| 7,071,806 B2 | 7/2006 | Masu et al. |
| 7,102,453 B1 | 9/2006 | Rohde et al. |
| 7,112,671 B2 | 9/2006 | Mody et al. |
| 7,241,630 B2 | 7/2007 | Hawkins et al. |
| 7,262,680 B2 | 8/2007 | Wang |
| 7,449,454 B2 | 11/2008 | Mody et al. |
| 7,486,168 B2 | 2/2009 | Kim |
| 7,557,566 B2 | 7/2009 | Kordonski et al. |
| 7,784,495 B2 | 8/2010 | Prakash et al. |
| 7,808,358 B2 | 10/2010 | Nakamura et al. |
| 7,888,929 B2 | 2/2011 | Kordonski et al. |
| 7,948,056 B2 | 5/2011 | Mi et al. |
| 7,951,582 B2 | 5/2011 | Gazit et al. |
| 8,026,716 B2 | 9/2011 | Makiranta et al. |
| 8,274,021 B2 | 9/2012 | Wang et al. |
| 8,378,669 B2 | 2/2013 | Wang et al. |
| 8,610,589 B2 | 12/2013 | Wang et al. |
| 8,878,684 B2 | 11/2014 | Wang et al. |
| 8,993,236 B2 | 3/2015 | Hajimiri et al. |
| 2001/0050555 A1 | 12/2001 | Hawkins et al. |
| 2002/0048534 A1 | 4/2002 | Storek et al. |
| 2002/0137121 A1 | 9/2002 | Rubinsky et al. |
| 2003/0012693 A1 | 1/2003 | Otillar et al. |
| 2003/0025639 A1 | 2/2003 | Rodney et al. |
| 2003/0027197 A1 | 2/2003 | Nikitin et al. |
| 2003/0059955 A1 | 3/2003 | Bamdad |
| 2003/0097165 A1 | 5/2003 | Krulevitch et al. |
| 2003/0169032 A1 | 9/2003 | Minchole et al. |
| 2004/0100277 A1 | 5/2004 | Tam |
| 2004/0171172 A1 | 9/2004 | Laitinen et al. |
| 2005/0079598 A1 | 4/2005 | Davis |
| 2005/0087000 A1 | 4/2005 | Coehoorn et al. |
| 2005/0106758 A1* | 5/2005 | Fukumoto ............ G01N 27/745 436/526 |
| 2005/0171574 A1 | 8/2005 | Rubinsky et al. |
| 2005/0221333 A1 | 10/2005 | Sundararajan et al. |
| 2005/0275497 A1 | 12/2005 | Ramadan et al. |
| 2006/0003371 A1 | 1/2006 | Russell et al. |
| 2006/0006884 A1 | 1/2006 | Yamada et al. |
| 2006/0020371 A1 | 1/2006 | Ham et al. |
| 2006/0193390 A1 | 8/2006 | Sedarat |
| 2006/0204699 A1 | 9/2006 | Maltezos et al. |
| 2006/0240416 A1 | 10/2006 | Banerjee et al. |
| 2007/0007486 A1 | 1/2007 | Gleich et al. |
| 2007/0172890 A1 | 7/2007 | Prins et al. |
| 2007/0197900 A1 | 8/2007 | Baudenbacher et al. |
| 2007/0287208 A1 | 12/2007 | Thompson et al. |
| 2008/0024117 A1 | 1/2008 | Hong et al. |
| 2008/0206104 A1 | 8/2008 | Prins et al. |
| 2008/0207464 A1 | 8/2008 | Prins et al. |
| 2008/0214092 A1 | 9/2008 | Kordonski et al. |
| 2008/0237843 A1 | 10/2008 | Gupta et al. |
| 2008/0258721 A1 | 10/2008 | Guo et al. |
| 2008/0286878 A1* | 11/2008 | Vezenov .................... 436/94 |
| 2008/0292870 A1* | 11/2008 | Das ................ 428/323 |
| 2008/0309329 A1 | 12/2008 | Kahlman et al. |
| 2008/0317632 A1 | 12/2008 | Shimasaki et al. |
| 2009/0029407 A1 | 1/2009 | Gazit et al. |
| 2009/0179316 A1 | 7/2009 | Wang et al. |
| 2009/0237844 A1 | 9/2009 | Duric et al. |
| 2009/0243603 A1 | 10/2009 | Makiranta et al. |
| 2009/0260692 A1 | 10/2009 | Walavalkar et al. |
| 2009/0267596 A1* | 10/2009 | Wang ................ G01R 33/1269 324/228 |
| 2010/0134097 A1 | 6/2010 | Wang et al. |
| 2010/0163545 A1 | 7/2010 | Wang et al. |

(56) References Cited

U.S. PATENT DOCUMENTS

| | | | |
|---|---|---|---|
| 2010/0216282 | A1 | 8/2010 | Wang et al. |
| 2010/0245100 | A1 | 9/2010 | Wang et al. |
| 2010/0255556 | A1 | 10/2010 | Hunt et al. |
| 2010/0267169 | A1 | 10/2010 | Hajimiri |
| 2011/0004096 | A1 | 1/2011 | Guo et al. |
| 2011/0115482 | A1 | 5/2011 | Wang et al. |
| 2011/0175602 | A1 | 7/2011 | Wang et al. |

FOREIGN PATENT DOCUMENTS

| | | |
|---|---|---|
| EP | 2060637 | 5/2009 |
| JP | 2002-005892 A | 1/2002 |
| WO | WO 97/42317 | 11/1997 |
| WO | WO 99/27133 | 6/1999 |
| WO | WO 99/54506 | 10/1999 |
| WO | WO 00/20040 | 4/2000 |
| WO | 2005/099419 | 10/2005 |
| WO | WO 2005/099419 | 10/2005 |
| WO | WO 2006/131892 | 12/2006 |
| WO | WO 2007/092909 | 8/2007 |
| WO | WO 2007092909 A2 * | 8/2007 |
| WO | 2007/122293 | 11/2007 |
| WO | 2007/132374 | 11/2007 |
| WO | WO 2007/122293 | 11/2007 |
| WO | WO 2007/132374 A1 | 11/2007 |

OTHER PUBLICATIONS

D.M. Pozar, Microwave Engineering, New York: J. Wiley & Sons, 1998.
D.R. Baselt, et al., "A Biosensor based on magnetoresistance Technology", Biosensor and Bioelectronics, vol. 13, Issue 7-8, pp. 731-739, Oct. 1998.
Florescu Octavian et al: "Fully integrated detection of single magnetic beads in complementary metal-oxide semiconductor", Journal of Applied Physics, American Institute of Physics. New York, US, vol. 103, No. 4, Feb. 19, 2008 (Feb. 19, 2008), pp. 46101-46101.
G. Li, et al., "Model and Experiment of Detecting Multiple Magnetic Nanoparticles as Biomolecular Labels by Spin Valve Sensors", *IEEE Transactions on Magnetics*, vol. 40, No. 4, pp. 3000-3002, Jul. 2004.
G.A. Gibson, et al., "Magnetic force microscope study of the micromagnetics of submicrometer magnetic particles", Journal of Applied Physics, vol. 73, issue 9, pp. 4516-4521, Jan. 1993.
Invitrogen Corporation, Custom Products and Services, Reliability, Quality, Partnership, Invitrogen custom turnkey solutions, 2006, pp. 1-22, (retrieved viahttps://tools.lifetechnologies.com/downloads/B-065997_Services-brochure.pdf on May 19, 2015).
Invitrogen Online Catalog as of Jul. 1, 2007 (retrieved via http://web.archive.org/web/20070701103739/https://catalog.invitrogen.com/index.cfm?fuseaction=userCountry.selectCountry&returnURL=https%3A%2F%2Fcatalog%2Einvitrogen%2Ecom%2Findex%2Ecfm%3F on May 19, 2015).
Kiely Jet Al: "Paramagnetic particle detection for use with an immunoassay based biosensor", IET Sci. Meas. Technol. vol. 1, No. 5, Sep. 6, 2007 (Sep. 6, 2007), pp. 270-275.
P.A. Besse, et al., "Detection of a single magnetic microbead using a miniaturized silicon Hall sensor", Applied Physics Letters, vol. 80, No. 22, pp. 4199-4201, Jun. 3, 2002.
Ramadan Q et al: "An integrated microfluidic platform for magnetic microbeads separation and confinement", Biosensors and Bioelectronics, Elsevier BV, NL, vol. 21, No. 9, Mar. 15, 2006 (Mar. 15, 2006), pp. 1693-1702.
S. Chikazumi, "Physics of Magnetism", Krieger, Malabar, FL, 1986.
S. Tanaka, et al., "A DNA Detection System Based Upon a High Tc SQUID and Ultra-Small Magnetic Particles", *IEEE Transaction on Applied Superconductivity*, vol. 15, No. 2, Jun. 2005, pp. 664-667.
Shu-Jen Han et al: "A High-Density Magnetoresistive Biosensor Array with Drift-Compensation Mechanism", 2007 IEEE International Solid-State Circuits Conference (IEEE CAT.N0.07CH37858), IEEE, Piscataway, NJ, USA, Feb. 1, 2007 (Feb. 1, 2007), pp. 168-169, 594.
T. Aytur, et al., "An Immunoassay Platform Based on CMOS Hall Sensors", *Solid-State Sensor, Actuator and Microsystems Workshop*, Jun. 2002, 4 pages.
Wang, H. Et al, IEEE International Solid-State Circuits Conference—Digest of Technical Papers Feb. 2009, 438-439 and 439a.
Biesecker et al, "Derivation of RNA aptamer inhibitors of human complement C5," Immunopharmacology (1999) vol. 42, Issue 1-3, pp. 219-30.
Blind et al., "Cytoplasmic RNA modulators of an inside-out signal-transduction cascade," Proc. Nat'l. Acad. Sci. USA, 96:3606-3610 (1999).
Boiziau et al. "DNA Aptamers Selected Against the HIV-1*trans*-Activation-responsive RNA Element Form RNA-DNA Kissing Complexes," Journal of biological chemistry (1999) vol. 274, Issue 18, pp. 12730-12737.
Boiziau et al., "Identification of Aptamers Against the DNA Template for In Vitro Transcription of the HIV-1 TAR Element," Antisense Nucleic Acid Drug Dev. (1997) vol. 7, Issue 4, pp. 369-380.
Brockstedt et al., "In vitro evolution of RNA aptamers recognizing carcinogenic aromatic amines," Biochem. Biophys. Res. Commun. (2004) vol. 313, Issue 4, pp. 1004-1008.
Brodeur et al., "Monoclonal Antibody Production Techniques and Applications," pp. 51-63, Marcel Dekker, Inc., New York, (1987).
Burke et al. "RNA aptamers to the adenosine moiety of S-adenosyl methionine: structural inferences from variations on a theme and the reproducibility of SELEX," Nucleic Acids Research (1997) vol. 25, Issue 10, pp. 2020-2024.
Daniels, "A tenascin-C aptamer identified by tumor cell SELEX: systematic evolution of ligands by exponential enrichment," PNAS (2003) vol. 100, Issue 26, pp. 15416-15421.
Duconge et al., "In vitro selection identifies key determinants for loop-loop interactions: RNA aptamers selective for the TAR RNA element of HIV-1," RNA (1999) vol. 5, Issue 12, pp. 1605-1614.
Ellington et al., "In vitro selection of RNA molecules that bind specific ligands," Nature 346, 818-22 (1990).
Eulberg et al., "Development of an automated in vitro selection protocol to obtain RNA-based aptamers: identification of a biostable substance P antagonist," Nucleic Acids Res. (2005) vol. 33, Issue 4, pp. e45.
Ferguson et al., "Application of free-energy decomposition to determine the relative stability of Rand S oligodeoxyribonucleotide methylphosphonates," Antisense Res Dev, 1991 Fall; 1(3):243-54.
Flinders et al., "Recognition of planar and nonplanar ligands in the malachite green-RNA aptamer complex," Chembiochem (2004) vol. 5, Issue 1, pp. 62-72.
Fukusaki et al., "DNA aptamers that bind to chitin," Bioorganic Med. Chem. Lett. (2000) vol. 10, Issue 5, pp. 423-425.
Gebhardt, "RNA aptamers to S-adenosylhomocysteine: kinetic properties, divalent cation dependency, and comparison with anti-S-adenosylhomocysteine antibody," Biochemistry (2000) vol. 39, Issue 24, pp. 7255-7265.
Geiger et al, "RNA aptamers that bind L-arginine with sub-micromolar dissociation constants and high enantioselectivity," Nucleic Acids Research (1996) vol. 24, Issue 6, pp. 2755-2758.
Gilbert et al. Bioorganic Med. Chem. (1997) vol. 5, Issue 6, pp. 1115-1122.
Gopinath et al., "An efficient RNA aptamer against human influenza B virus hemagglutinin," J Biochem (Tokyo) (2006) vol. 139, Issue 5, pp. 837-846.
Haller et al., "In vitro selection of a 7-methyl-guanosine binding RNA that inhibits translation of capped mRNA molecules," PNAS (1997) vol. 94, Issue 16, pp. 8521-8526.
Hardwidge et al., "Charge neutralization and DNA bending by the *Escherichia coli* catabolite activator protein," Nucleic Acids Res, May 1, 2002; 30(9): 1879-85.

(56) References Cited

OTHER PUBLICATIONS

Hesselberth et al., "In Vitro Selection of RNA Molecules That Inhibit the Activity of Ricin A-chain," Journal of Biological Chemistry (2000) vol. 275, Issue 7, pp. 4937-4942.
Hicke et al., "Tenascin-C Aptamers Are Generated Using Tumor Cells and Purified Protein," J. Biol. Chem. (2001) vol. 276, Issue 52, pp. 48644-48654.
Hirao et al., "RNA: Structure Metabolism and Catalysis," Journal of Biological Chemistry (2000) vol. 275, Issue 7, pp. 4943-4948.
Hornung et al., "In vitro selected RNA molecules that bind to elongation factor Tu," Biochemistry (1998) vol. 37, Issue 20, pp. 7260-7267.
Huizenga et al., "A DNA Aptamer That Binds Adenosine and ATP," Biochemistry, 34:656-665 (1995).
Jakobovits et al., "Germ-line transmission and expression of a human-derived yeast artificial chromosome," Nature 362, 255-258 (1993).
Jakobovits et al., "Analysis of homozygous mutant chimeric mice: deletion of the immunoglobulin heavy-chain joining region blocks B-cell development and antibody production," Proc. Natl. Acad. Sci. USA (90)6: 2551-2555 (1993).
Jeong et al., "In Vitro Selection of the RNA Aptamer against the Sialyl Lewis X and Its Inhibition of the Cell Adhesion ," Biochemical and Biophysical Research Communications (2001) vol. 281, Issue 1, pp. 237-243.
Kato et al., "In vitro selection of DNA aptamers which bind to cholic acid," Biochim. Biophys. Acta (2000) vol. 1493, Issue 1-2, pp. 12-18.
Kibler-Herzog et al., "Duplex stabilities of phosphorothioate, methylphosphonate, and RNA analogs of two DNA 14-mers," Nucleic Acids Res, Jun. 11, 1991; 19(11):2979-86.
Kimoto et al., "Anti-(Raf-1) RNA aptamers that inhibit Ras-induced Raf-1 activation ," Eur. J. Biochem. (2002) vol. 269, Issue 2, pp. 697-704.
Kimoto et al., "RNA aptamers that specifically bind to the Ras-binding domain of Raf-1," FEBS Lett. (1998) vol. 441, Issue 2, pp. 322-326.
Kirchhoff et al. (2001) J. Combinatorial Chem., 3: 71-77.
Kohler et al., "Continuous cultures of fused cells secreting antibody of predefined specificity," Nature, 256:495-497 (1975).
Koizumi et al., "Molecular recognition of cAMP by an RNA aptamer," Biochemistry (2000) vol. 39, Issue 30, pp. 8983-8992.
Kozbor, J. "A human hybrid myeloma for production of human monoclonal antibodies," Immunol. 133: 3001 (1984).
Kraus et al, J. "Cutting Edge: Novel RNA Ligands Able to Bind CD4 Antigen and Inhibit CD4+T Lymphocyte Function," Immunol. (1998) vol. 160, Issue 11, pp. 5209-5212.
Le Bee et al., "Stereospecific Grignard-Activated Solid Phase Synthesis of DNA Methylphosphonate Dimers," J Org Chem, Jan. 26, 1996; 61(2):510-513.
Legiewicz et al., "A More Complex Isoleucine Aptamer With a Cognate Triplet," J. Biol. Chem. published online Mar. 16, 2005.
Lin et al., "Use of EDTA derivatization to characterize interactions between oligodeoxyribonucleoside methylphosphonates and nucleic acids,"Biochemistry, Feb. 7, 1989; 28(3):1054-61.
Liu, et al., "RNA aptamers specific for bovine thrombin," Journal of Molecular Recognition (2003) vol. 16, Issue 1, pp. 23-27.
Lorsch et al., "In vitro selection of RNA aptamers specific for cyanocobalamin," Biochemistry, (33)4:973-82 (1994).
Lozupone et al., "Selection of the simplest RNA that binds isoleucine," RNA (2003) vol. 9, Issue 11, pp. 1315-1322.
Mannironi et al., "In Vitro Selection of Dopamine RNA Ligands," Biochemistry (36)32:9726 (1997).
Marcus-Sekura et al., "Comparative inhibition of chloramphenicol acetyltransferase gene expression by antisense oligonucleotide analogues having alkyl phosphotriester, methylphosphonate and phosphorothioate linkages," Nucleic Acids Res, Jul. 24, 1987; 15(14):5749-63.
McCafferty et al., "Phage antibodies: filamentous phage displaying antibody variable domains," Nature 348, 552-553 (1990).
Mendez et al. "Functional transplant of megabase human immuno-globulin loci recapitulates human antibody response in mice," Nature Genetics (15)2: 146-156 (1997).
Mendonsa et al., "In vitro selection of aptamers with affinity for neuropeptide Y using capillary electrophoresis," J. Am. Chem. Soc. (2005) vol. 127, Issue 26, pp. 9382-9383.
Misono et al. "Selection of RNA aptamers against human influenza virus hemagglutinin using surface plasmon resonance ," Anal. Biochem. (2005) vol. 342, Issue 2, pp. 312-317.
Munson et al., "Ligand: a versatile computerized approach for characterization of ligand-binding systems," Anal. Biochem., (107)1:220 (1980).
Nielsen et al., "An introduction to peptide nucleic acid," Curr Issues Mol Biol, 1999; 1(1-2):89-104.
Nielsen, "DNA analogues with nonphosphodiester backbones," Annu. Rev. Biophys. Biomol. Struct, 1995; 24:167-83.
Okonogi et al., "Phosphate backbone neutralization increases duplex DNA flexibility: A model for protein binding," PNAS U.S.A., Apr. 2, 2002; 99(7):4156-60.
Pini et al., "Phage display of antibody fragments," Curr. Protein Pept. Sci., 1(2): 155-69 (2000).
Ray et al., "Peptidenucleic acid (PNA): its medical and biotechnical applications and promisefor the future," FASEB J., Jun. 2000; 14(9): 1041-60.
Reynolds et al., "Synthesis and thermodynamics of oligonucleotides containing chirally pure R(P) methylphosphonate linkages," Nucleic Acids Res, Nov. 15, 1996; 24(22):4584-91.
Roychowdhury-Saha et al., "Flavin recognition by an RNA aptamer targeted toward FAD," Biochemistry (2002) vol. 41, Issue 8, pp. 2492-2499.
Ruckman, et al. "Nucleic Acids, Protein Synthesis, and Molecular Genetics," J. Biol. Chem. (1998) vol. 273, Issue 32, pp. 20556-20567.
Saran et al. "The tyranny of adenosine recognition among RNA aptamers to coenzyme a," BMC Evol. Biol. (2003) vol. 3, Issue 1, pp. 26.
Schneider et al, "Selective enrichment of RNA species for tight binding to *Escherichia coli* rho factor," FASEB J. (1993) vol. 7, Issue 1, pp. 201-207.
Sung et al., "Synthesis of the human insulin gene. Part II. Further inprovements in the modified phosphotriester method and the synthesis of seventeen deoxyribooligonucleotide gragments constituting human insulin chains B and mini-cDNA," Nucleic Acids Res, Dec. 20, 1979: 7(8):2199-212.
Tahiri-Alaoui et al., "High affinity nucleic acid aptamers for streptavidin incorporated into bi-specific capture ligands," Nucleic Acids Res. (2002) vol. 30, Issue 10, pp. e45.
Takeno et al., "Selection of an RNA Molecule That Specifically Inhibits the Protease Activity of Subtilisin," Journal of Biochemistry (1999) vol. 125, Issue 6, pp. 1115-1119.
Tao et al., "Arginine-binding RNAs resembling TAR identified by in vitro selection," Biochemistry (1996) vol. 35, Issue 7, pp. 2229-2238.
Rusconi et al. "Blocking the initiation of coagulation by RNA aptamers to factor Vlla," Thromb Haemost. (2000) vol. 84, Issue 5, pp. 841-848.
Tuerk et al., "Systematic evolution of ligands by exponential enrichment: RNA ligands to bacteriophage T4 DNA polymerase," Science 249, 505-10 (1990).
Ulrich et al., "In vitro selection of RNA molecules that displace cocaine from the membrane-bound nicotinic acetylcholine receptor," Proc. Natl. Acad. Sci. USA (1998) vol. 95, Issue 24, pp. 14051-14056.
Urvil et al., "Selection of RNA Aptamers that Bind Specifically to the NS3 Protease of Hepatitis C Virus," European Journal of Biochemistry (1997) vol. 248, Issue 1, pp. 130-138.
Van Boom et al., "Synthesis of oligonucleotides with sequences identical with or analogous to the 3'-end of 16S ribosomal RNA of *Escherichia coli*: preparation of m-6-2-A-C-C-U-C-C and A-C-C-U-C-m-4-2C via phosphotriester intermediates," Nucleic Acids Res, Mar. 1977; 4(3):747-59.
Vyazovkina et al., "Synthesis of specific diastereomers of a DNA methylphosphonate heptamer, (CpCpApApApCpA), and stability

(56) References Cited

OTHER PUBLICATIONS of base pairing with the normal DNA octamer (TPGPTPTPTPGPGPC)," Nucleic Acids Res, Jun. 25, 1994; 22(12):2404-9.

Wallace et al., "In vitro selection and characterization of streptomycin-binding RNAs: recognition discrimination between antibiotics," RNA (1998) vol. 4, Issue 1, pp. 112-123.

Wang et al., "RNA molecules that specifically and stoichiometrically bind aminoglycoside antibiotics with high affinities," Biochemistry (1996) vol. 35, Issue 38, pp. 12338-12346.

Win et al., "Codeine-binding RNA aptamers and rapid determination of their binding constants using a direct coupling surface plasmon resonance assay," Nucleic Acids Res. (2006) vol. 34, Issue 19, pp. 5670-5682.

Vaish et al., "A novel, modification-dependent ATP-binding aptamer selected from an RNA library incorporating a cationic functionality," Biochemistry (2003) vol. 42, Issue 29, pp. 8842-8851.

Yang et al., "DNA ligands that bind tightly and selectively to cellobiose," PNAS (1998) vol. 95, Issue 10, pp. 5462-5467.

Disney et al., "Targeting a Pneumocystis carinii group I intron with methylphosphonate oligonucleotides: backbone charge is not required for binding or reactivity," Biochemistry, Jun. 13, 2000; 39(23):6991-7000.

Thiviyanathan et al., "Structure of hybrid backbone methylphosphonate DNA heteroduplexes: effect of R and S stereochemistry," Biochemistry, Jan. 22, 2002; 41(3):827-38.

Goding, James W., "Monoclonal Antibodies: Principles and Practice," Third Edition, pp. 50-115, 1996, Academic Press.

Harlow, E., and Lane, D., "Antibodies: A Laboratory Manual," 1988, Cold Springs Harbor Laboratory, Cold Springs Harbor, N.Y.

Hermanson, "Bioconjugate Techniques," Elsevier (2008).

Hozumi et al., "Vapor phase formation of a well-ordered aldehyde-terminated self-assembled monolayer on a $SiO_2$ surface and formation of silver film on the surface based on the silver mirror reaction," Surface Science 600, pp. 4044-4047, 2006.

\* cited by examiner

LOW COST, PORTABLE SENSOR FOR MOLECULAR ASSAYS

CROSS-REFERENCE TO RELATED APPLICATIONS

This application is a continuation-in-part of patent application Ser. No. 12/762,229 filed Apr. 16, 2010 and published as US 2010-0267169 A1 which application claimed priority to and the benefit of then co-pending U.S. provisional patent application Ser. No. 61/170,547, filed Apr. 17, 2009, and this application claims priority to and the benefit of co-pending U.S. provisional patent application Ser. No. 61/414,605 filed Nov. 17, 2010, each of which applications is incorporated herein by reference in its entirety. This application is also related to U.S. patent application Ser. No. 12/399,603 filed Mar. 6, 2009 and published as US 2009-0267596 A1, U.S. patent application Ser. No. 12/559,517 filed Sep. 15, 2009 and published as US 2010-0134097 A1, U.S. patent application Ser. No. 12/710,334 filed Feb. 22, 2010 and published as US 2010-0245100 A1, U.S. patent application Ser. No. 12/713,128 filed Feb. 25, 2010 and published as US 2010-0216282 A1, U.S. patent application Ser. No. 12/830,975 filed Jul. 6, 2010 and published as US 2011-0004096 A1, U.S. patent application Ser. No. 12/959,331 filed Dec. 2, 2010 and published as US 2011-0115482 A1, and U.S. patent application Ser. No. 12/978,296 filed Dec. 23, 2010 and published as US 2011-0175602 A1, each of which applications is incorporated herein by reference in its entirety.

FIELD OF THE INVENTION

The invention relates to sensors in general and particularly to a sensor that can identify specific chemical sequences.

BACKGROUND OF THE INVENTION

Microarray systems are widely used for drug discovery, life science research, and clinical diagnostics. Future development of this technology is directed towards Point-of-Care (POC) applications including diagnosing disease, tracking epidemic disease outbreak, detecting biological and chemical weapons and hazardous conditions, and forensic analysis. However, these applications are limited due to the lack of instruments that provide hand-held portability, high sensitivity, low cost, and low battery power consumption. These problems stem from the current modality of fluorescent detection using costly and bulky optics.

The technology of sensing molecular species such as segments of, or entire strands of, nucleic acids such as DNA and RNA generally rely on optical methods in which an input optical signal interacts with chemical substances (known as probes) attached to known locations on a chip (such as a so-called gene chip). The optical response signal is received and analyzed, and depending on the response, an interaction of the probe with a target substance (e.g., a molecule having a complementary chemical sequence to a sequence on the probe) can be elucidated. The result can be used to determine whether an interaction of a known probe has or has not occurred with a specimen of interest, which can be used to determine whether the specimen of interest does or does not contain a specific target sequence or molecule.

In the prior art, it is necessary to have a source of the input optical signal which may include one or more specific wavelengths that interact with known probes, either alone or with optical sensitizing substances. In order to obtain the necessary wavelengths with sufficient purity, it is common to have to use optical processing techniques that rely on optical filters, optical diffraction, and/or multiple optical sources in order to provide suitable input optical signals at the specific wavelengths needed. In addition, it is necessary to have optical detectors that respond to the correct wavelengths that indicate the presence or absence of the target substances. In order to have a plurality of substance tests performed on a single chip, it is also often necessary to provide lenses (or arrays of lenses) that allow one to interrogate a plurality of known physical locations on the chip. All of the required optical technology that is needed adds significant cost and complication to the operation of optical systems and methods of testing for chemical substances in specimens of interest.

There is a need for systems and methods of analyzing specimens of interest for the presence or absence of chemical substances that avoid the complications and the costs associated with optical detection methods.

SUMMARY OF THE INVENTION

According to one aspect, the invention features a non-optical chemical sensor system. The system comprises a sensor structure having a surface, the sensor structure configured to measure a distance of a label from the sensor structure surface; a tether comprising a probe strand of a chemical substance having binding sites disposed along a length of the probe strand, the probe strand having a first end attached to the surface of the sensor structure and having a second end; a control and analysis module connected to the sensor structure, the control and analysis module configured to control a non-optical measurement signal applied to the sensor structure and to analyze a measurement signal generated by the sensor structure; and at least one label, the at least one label configured to be sensed non-optically by the sensor; the control and analysis module configured to provide a measurement result indicative of the presence of a target chemical compound, the measurement result based on a first measurement of a distance of the label from the surface of the sensor in the absence of the target chemical compound and a second measurement of the distance of the label from the surface of the sensor in the presence of the target chemical compound.

In one embodiment, the at least one label is connected to the second end of the tether.

In another embodiment, the non-optical measurement signal is a magnetic signal.

In yet another embodiment, the non-optical measurement signal is an electrical signal.

In still another embodiment, the measurement result is represented by a change in a frequency.

In a further embodiment, the label is configured to be subjected to a deliberately applied force.

In yet a further embodiment, the probe strand comprises a ribonucleic acid.

In an additional embodiment, the probe strand comprises a polymer.

According to another aspect, the invention relates to a non-optical method of performing a chemical assay. The method comprises the steps of: providing a non-optical chemical sensor system; making a first measurement of the distance of the label from the surface of the sensor in the absence of a specimen of interest; applying a fluid comprising the target chemical to be identified to the non-optical chemical sensor system; making a second measurement of the distance of the label from the surface of the sensor in the presence of the specimen of interest; providing a measurement result indicative of the presence of a target chemical compound in the specimen of interest, the measurement result based on the first measurement and the second measurement; and performing at least one of recording the result, transmitting the result to a data handling system, or to displaying the result to a user. The a non-optical chemical sensor system comprises a sensor structure having a surface, the sensor structure configured to measure a distance of a label from the sensor structure surface; a tether comprising a probe strand of a chemical substance having binding sites disposed along a length of the probe strand, the probe strand having a first end attached to the surface of the sensor structure and having a second end; a control and analysis module connected to the sensor structure, the control and analysis module configured to control a non-optical measurement signal applied to the sensor structure and to analyze a measurement signal generated by the sensor structure; and at least one label, the at least one label configured to be sensed non-optically by the sensor; the control and analysis module configured to provide a measurement result indicative of the presence of a target chemical compound, the measurement result based on a first measurement of a distance of the label from the surface of the sensor in the absence of the target chemical compound and a second measurement of the distance of the label from the surface of the sensor in the presence of the target chemical compound.

In one embodiment, the at least one label is connected to the second end of the tether.

In another embodiment, the non-optical measurement signal is a magnetic signal.

In yet another embodiment, the non-optical measurement signal is an electrical signal.

In still another embodiment, the measurement result is represented by a change in a frequency.

In a further embodiment, the label is configured to be subjected to a deliberately applied force.

In yet a further embodiment, the probe strand comprises a ribonucleic acid.

In an additional embodiment, the probe strand comprises a polymer.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 4A, FIG. 4B and FIG. 4C illustrate an embodiment of a method in which the looping is combined with a force deliberately applied to the label.

DETAILED DESCRIPTION

Figures 1A, 1B:
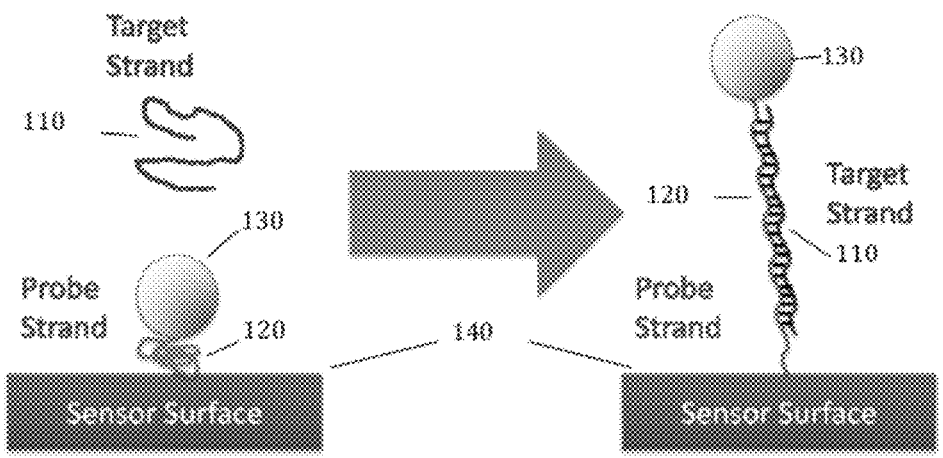
FIG. 1A and FIG. 1B illustrate an embodiment of a method in which a single-strand of DNA that is covalently attached to the surface of the chip on one end, and a magnetic bead on the other.

A label-free molecular assay system and associated methods are described. These systems and methods are expected to meet the needs expressed previously, and to overcome the limitations previously mentioned. The approach described utilizes the magnetic and/or electrical sensing of the position of a label, such as a magnetic bead (or magnetic particle), functionalized to an integrated circuit chip. No optical methods are required, and optical components such as those used in the prior art are absent in the apparatus described hereinbelow.

Sensor Component

An enabling component of our POC device is a detection device and a detection method for a label, such as a magnetic bead or particle. U.S. Patent Application Publication Nos. 2009-0267596 A1, 2010-0163545 A1, 2010-0134097 A1, 2010-0216282 A1, 2011-0004096 A1, 2011-0115482 A1 and 2011-0175602 A1 describe enabling technology that provides magnetic sensors that can detect the presence of magnetic beads.

Several related applications, including co-pending U.S. patent application Ser. Nos. 12/399,603, 12/399,320, and 12/559,517, described sensing components (also referred to as "detectors") which can be used to manufacture systems that can detect from one to many magnetic particles, such as for example, microscopic magnetic particles which can be captured by molecules. Sensor systems that can detect and/or count small magnetic particles in a sample are suitable for use in a wide variety of analysis and diagnostic equipment, such as for example, medical diagnostic instruments. When some or all of such systems are integrated onto one or more substrates, these sensor systems can be used to manufacture medical diagnostic instruments, such as relatively small portable low power battery powered medical diagnostic instruments.

U.S. patent application Ser. No. 12/978,296 describes a general detection platform for sensing a magnetic and/or an electrical energy change or at least one of an electrical property and a magnetic property of an object of interest, such as a particle. Sensing a magnetic and/or an electrical energy change has been used widely as a detection method in sensor area. This magnetic and/or electrical energy change is often captured by the resonance frequency-shift of a designed LC sensing tank. LC oscillator based frequency-shift sensing is shown to be an ultrasensitive sensing scheme to detect the magnetic and/or electrical energy change, caused by the test samples. Based on the noise floor study of the LC oscillator based sensor, a noise cancellation method is also described which increases the sensor SNR without power overhead. The LC oscillator based frequency-shift sensing and the noise cancellation method form a general detection ultrasensitive platform for advanced sensor design which detects magnetic and/or electrical energy change. Applications in biosensing are contemplated, among other possible uses. In some embodiments, one sensor of a plurality of sensors measures electrically and a different sensor of the plurality of sensors measures magnetically. In some embodiments, the same sensor measures electrically and magnetically in two different measurement intervals. In some embodiments, the same sensor measures electrically and magnetically in the same measurement interval.

U.S. patent application Ser. No. 12/978,296 describes several embodiments of new inductor structures that have a substantially uniform magnetic field strength in the near-field. Such structures have a highly uniform magnetic near-field field and are particularly well suited for fabrication as integrated structures. Thus, these new types of inductors solve the problem of how to generate a polarization magnetic field that can provide a substantially uniform transducer gain. Since these inductors can be manufactured as integrated structures, they are particularly suitable for use in small portable low power biological and/or medical magnetic particle sensing systems.

In the present application, the term "label" will be used generally to denote a particle that can be attached to a chemical substance, such that a sense property of the label changes as a function of the distance of the label from the location of a sensor on the surface of the die. Some particles may have properties such as magnetic properties or electrical properties that are amenable to be measured by the sensor.

In one embodiment, a sensor is contemplated that is comprised of a silicon CMOS on-chip inductor that is coupled to an oscillator, characterized by a resonant frequency. In one embodiment, perturbation of the inductor's magnetic field by a magnetic bead leads to a shift in the oscillator's frequency. The sensor is not only sensitive to the presence or absence of beads, but also to the bead's distance from the surface of the die, measured along a line normal to the surface. The normal distance dependence can be used for several sensing configurations.

Additionally, sensing may not be limited to the magnetic properties of the label. Sensing can be performed using additional properties of the label, such as electric charge, conductivity, or magnetic relaxation. Other properties can provide a basis for detection, as long as a change in signal can be distinguished with a change in the distance of the particle from the surface of the die. A sensor can be constructed to sense using a variety of electrical or magnetic methods. For example, in one embodiment, a capacitive structure can be fabricated on a chip or surface to detect changes in capacitance due to the proximity of the label to the surface. In another embodiment, an antenna can be fabricated to emit electrical radiation to the label. The energy absorbed or reflected by the label can be used for detection. In yet another embodiment, the magnetic coupling between two inductors can be used to detect a magnetic label. As another embodiment, magnetic labels can be constructed with differing magnetic or electrical relaxation time. The oscillator can sweep several frequencies to obtain multiplexed detection of labels.

Various molecules can be detected using several sensing schemes. Some of the possible sensing schemes will be discussed:

Label-Free DNA Hybridization Assay

It is advantageous if a POC hybridization assay requires minimal target sample preparation to improve ease-of-use, to speed up diagnosis, and to reduce the cost of the system both by minimizing expensive reagents and operational labor. Therefore a preferred embodiment involves a label-free system or method that does not require the functionalization of target DNA to a biomarker.

In the present embodiments, non-covalent attachment of the probe strand to the sensor and the bead was investigated and deemed inadequate for stability reasons. To detect the complementary strand in a target sample (which can be a sample of biological interest such as one comprising blood, cell lysate, or other biological material), the sample is introduced to the sensor site in a fluid that can be manipulated using microfluidic methods and that is in contact with a surface of a sensor, e.g., on top of an inductor. In some embodiments, upon hybridization, the persistence length of the probe strand increases from 4 nm to 50 nm. This change in dimension can cause the DNA probe strand to stand "erect" and "loiter" in regions further from the chip surface. Multiple tethers can be attached on the sensor site to increase the signal. Moreover, in an array having a plurality of sensor sites, each sensor site can be functionalized with a different probe strand to permit multiplexed detection of different targets.

First Embodiment

In one embodiment, this can be accomplished by utilizing the differing polymer properties of single stranded and double stranded DNA. A first embodiment is illustrated in FIG. 1A and FIG. 1B.

In the following embodiments, DNA will be used as an example of a chemical substance that is present in the form of a strand. However, it is contemplated that chemical substances of other kinds, such as other ribonucleic acids or strands of polymers having defined binding sites disposed along the length of the strand which binding sites are known to bind to specific molecules or chemical moieties, can also be used. A more thorough discussion of DNA and RNA sensing is provided hereinafter.

As illustrated in FIG. 1A, a probe strand 120, which can be single-strand of DNA, is covalently attached to the surface 140 of the sensor chip on one end, and to a magnetic bead 130 on the other end. In FIG. 1A, the probe strand 120 is present in a coiled or otherwise bent configuration. The magnetic bead 130 is separated from the surface 140 of the sensor by a short distance. Also shown in FIG. 1A is a target strand 110, which is present in a fluid medium that is in contact with the sensor. The target strand 110 is a substance, such as a segment of DNA that is complementary to at least a portion of the probe strand 120 that can bond with the probe strand. Such a target strand 110 will also be referred to as a "complemetary strand." Other target strands, that do not have chemistry that is compatible with binding with the probe strand 120 (and which may be referred to as "non-complementary strands"), may also be (and usually are) present in the fluid in contact with the sensor surface 140.

As illustrated in FIG. 1B, when a complementary target strand such as 110 is present, the target strand 110 and the probe strand 120 can bind chemically (for example by covalent bonding, by VanDerWaals bonding, or by electrostatic bonding). When such binding takes place, the conformation of the probe strand 120 can change from the coiled conformation as in FIG. 1A to a more linear conformation as illustrated schematically in FIG. 1B. With DNA, the well-known double helix structure can be generated from two DNA segments that have complementary nucleic bases. In the case of polymers, possible interactions could include cross-linking of two polymer sequences, one in each of the probe strand 120 and the target strand 110. After the interaction of the two strands 110 and 120, the structure between the bead 130 and the sensor surface 140 includes at least one segment that is linear rather than coiled, so that the distance between the bead 130 and the sensor surface 140 increases as compared to the distance between the bead 130 and the sensor surface 140 that is present in FIG. 1A. As will be described in greater detail hereinbelow, the sensor can be used to detect the change in distance between the bead 130 and the sensor surface 140, so that one can deduce that the probe strand 120 and the target strand 110 are complementary and have bonded. This provides a signal that can be interpreted as the presence of a target strand 110 that is complementary to the probe strand 120 in the fluid in contact with the sensor 140.

Second Embodiment

Figures 2A, 2B, 2C:
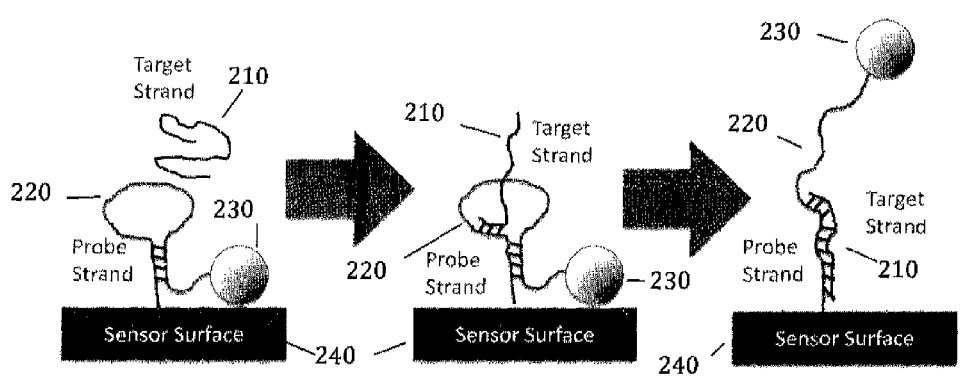
FIG. 2A, FIG. 2B and FIG. 2C illustrate an embodiment of a method in which a label that is tethered to the sensor surface is used. The label has a hybridized region, and an open loop region.

Other label-free sensing schemes can be accomplish the same goal. In FIG. 2A, a label (bead 230) is tethered to the sensor surface 240 with a probe strand 220 that has a hybridized region and an open loop region. Both the open loop region and the hybridized region contain sites that bind to the DNA target strand 210. In FIG. 2A the label (bead 230) is close to the sensor surface 240.

As shown in FIG. 2B, upon hybridization of the target strand 210 to a complementary region in the open loop of the DNA probe strand 220, the target strand 210 initiates a branch migration, thus unbinding the probe strand 220. The unbounded portion of the probe strand 220 moves away from the sensor surface 240 by Brownian motion, or under the influence of some deliberately applied force (e.g., a force supplied by a magnet or a voltage source).

As illustrated in FIG. 2C, the probe strand 220 and the target strand 210 bind to each other and the label (bead 230) is free to move to a location that is at a greater distance from the sensor surface 240 than the distance between the bead 230 and the sensor surface 240 as in FIG. 2A. As described in the first embodiment, the sensor is configured to sense the change in distance between the label and the sensor surface 240, and such a change signals the presence of a target 210 that is complementary to the probe 220.

Third Embodiment

Figures 3A, 3B:
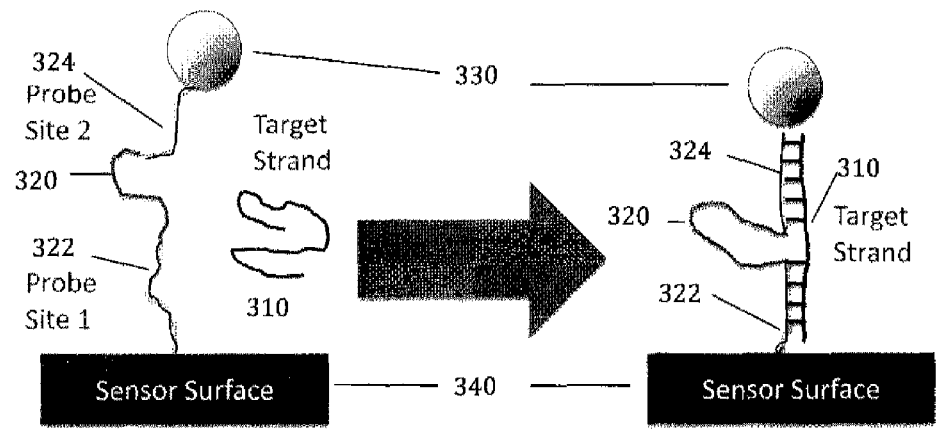
FIG. 3A and FIG. 3B illustrate an embodiment of a method in which a DNA looping scheme is used, in which the probe strand contains sites complementary to the target strand.

In a DNA looping scheme, as illustrated in FIG. 3A, FIG. 3B and FIG. 3C, the probe strand 320 contains multiple sites 322, 324 that are complementary to regions of the target strand 310. The probe strand has a bead 330 attached at one end and is attached to the sensor surface 340 at the other end.

As illustrated schematically in FIG. 3B, upon hybridization of the target strand 310 with the regions 322 and 324 of the probe strand 320, the middle section of the probe strand 320 forms a loop. The label (which can be a magnetic bead 330) is held in a location that is closer to the sensor surface 340 than the distance between the label (bead 330) and the sensor surface 340 as present in FIG. 3A. As described in the first embodiment, the sensor is configured to sense the change in distance between the label and the sensor surface 340, and such a change signals the presence of a target 310 that is complementary to the probe 320.

Fourth Embodiment

Figures 4A, 4B:
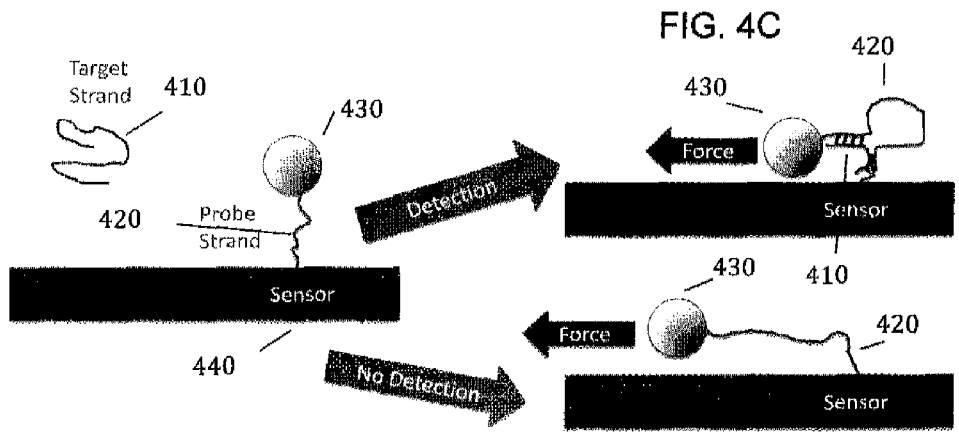

In another embodiment, the looping can be combined with a force deliberately applied to the label, such as a magnetic attraction or a fluidic flow. In FIG. 4A a probe strand 420 has a label 430 attached at one end and is attached at the other end to the sensor surface 440. A target strand 410 that can bind to the probe strand 430 is also shown.

In FIG. 4B the target strand 410 binds with the probe strand 420 so as to form a loop, in a manner similar to the interaction between target 310 and 320 in FIG. 3B. Under the influence of a force, indicated by the arrow labeled "Force," the label 430 is pushed to one side. However, because the binding between the target strand 410 and the probe strand 420 shortens the distance that the label 430 can move, the label remains within the detection distance of the sensor 440. In this embodiment, because the end of the looped strand remains in the vicinity of the sensor, the label 430 will be detected as being close to the sensor surface 440.

In FIG. 4C no binding between the probe strand 420 and a target strand 410 occurs. Under the influence of the applied force, again illustrated by an arrow labeled "Force," the label 430 moves away from the sensor, and is not detected.

As described in the first embodiment, the sensor is configured to sense the change in distance between the label and the sensor surface 440, and such a change signals the presence of a target 410 that is complementary to the probe 420. In the instance where the label is moved away from the sensor by a sufficient distance, the sensor senses that the label is not present.

Fifth Embodiment

Figures 5A, 5B:
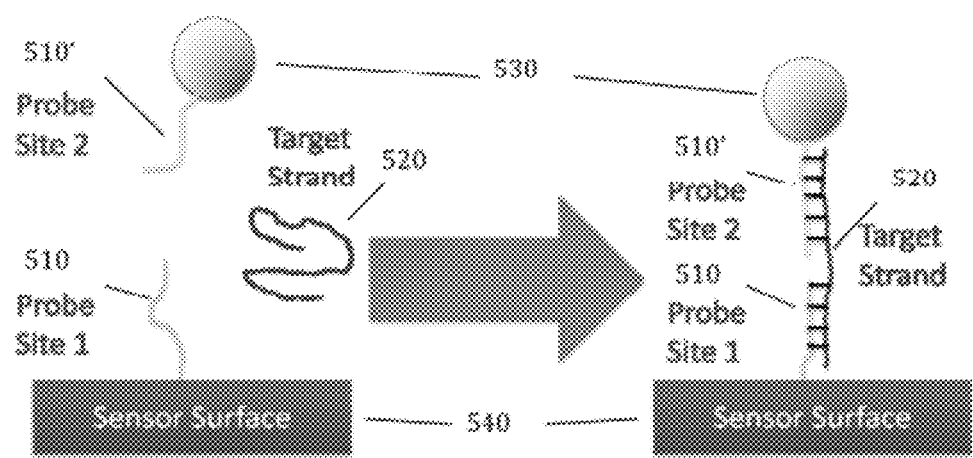
FIG. 5A and FIG. 5B illustrate an embodiment of a method in which a labeled version of the sensing scheme, similar to an Elisa Assay, is used.

FIG. 5A and FIG. 5B illustrate an embodiment of a method in which a labeled version of the sensing method, similar to an Enzyme-Linked Immunosorbent Assay (ELISA) Assay. This is similar to the embodiment illustrated in FIG. 3A and FIG. 3B, without the linker region in the middle of the probe strand. In FIG. 5A two probe strands, one 510 attached to the sensor surface 540 and one 510' attached to a label 530, are in solution with the target strand 520. As illustrated schematically in FIG. 5B, upon hybridization of the target strand 520 to both probe strands 510, 510', the label 530 is tethered to the sensor surface 540. As described in the first embodiment, the sensor is configured to sense the change in distance between the label and the sensor surface 540, and such a change signals the presence of a target 520 that is complementary to both of the probe strands 510, 510'.

Although sensing embodiments for DNA have been described, the embodiments are capable of being extended to RNA through similar functionalization in hybridization. Moreover, hybridization binding can be replaced with antibodies to initiate the binding events. The labels for use can be of varying size and properties. Because versions of the sensor can be integrated on a CMOS or integrated circuits chip, detection and processing can occur on the same die. However, sensor need not be monolithically integrated on a chip.

Sensor Operation

An integrated sensor has been developed that is capable of discriminating the distance of a label from the sensor. The label is attached to a single or group of probe molecules that interacts with a single or group of target molecules. As a consequence of this interaction, the probe molecule and/or the target molecule undergo a conformal change. This conformal change leads to perturbations in the distance of the label from the sensor. Thus, measurements and properties such as the concentration and the identity of one or more target molecules can be discerned from signals generated by the sensor (or by a plurality of sensors in a sensor array) and subjected to analysis using general purpose programmable computers programmed with suitable software that controls the analytical process, and such measurements and properties can be provided as a result of the analysis. Commercial software packages, such as LabView® available from National Instruments Corporation, 11500 N Mopac Expwy, Austin, Tex. 78759-3504, can handle the data collection and data processing. Results provided can be recorded, can be displayed to a user, or can be transmitted for use by another measurement or analytical process.

Figure 6:
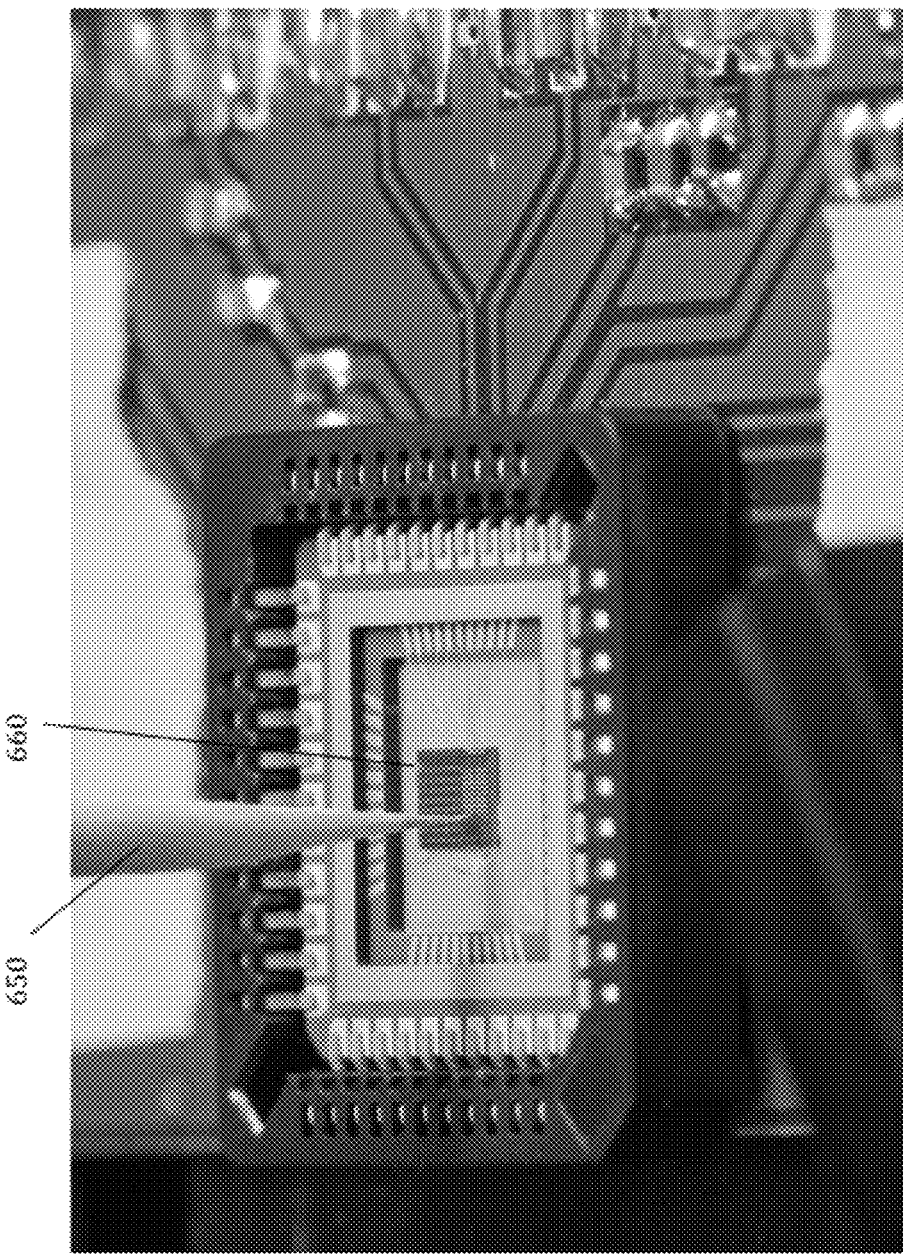
FIG. 6 is an image illustrating a test setup used to test the vertical sensitivity of the sensor.

FIG. 6 is an image illustrating a test setup used to test the vertical sensitivity of the sensor. As illustrated in FIG. 6, a non-magnetic support 650 was coated with magnetic beads and was positioned over the sensor surface 660. Using a micromanipulator having micrometer resolution, the non-magnetic support was moved vertically relative to the sensor surface. As a control, a non-magnetic support without a magnetic bead coating was also moved over the sensor. The signal from the sensor was recorded as a function of vertical position.

Figure 7:
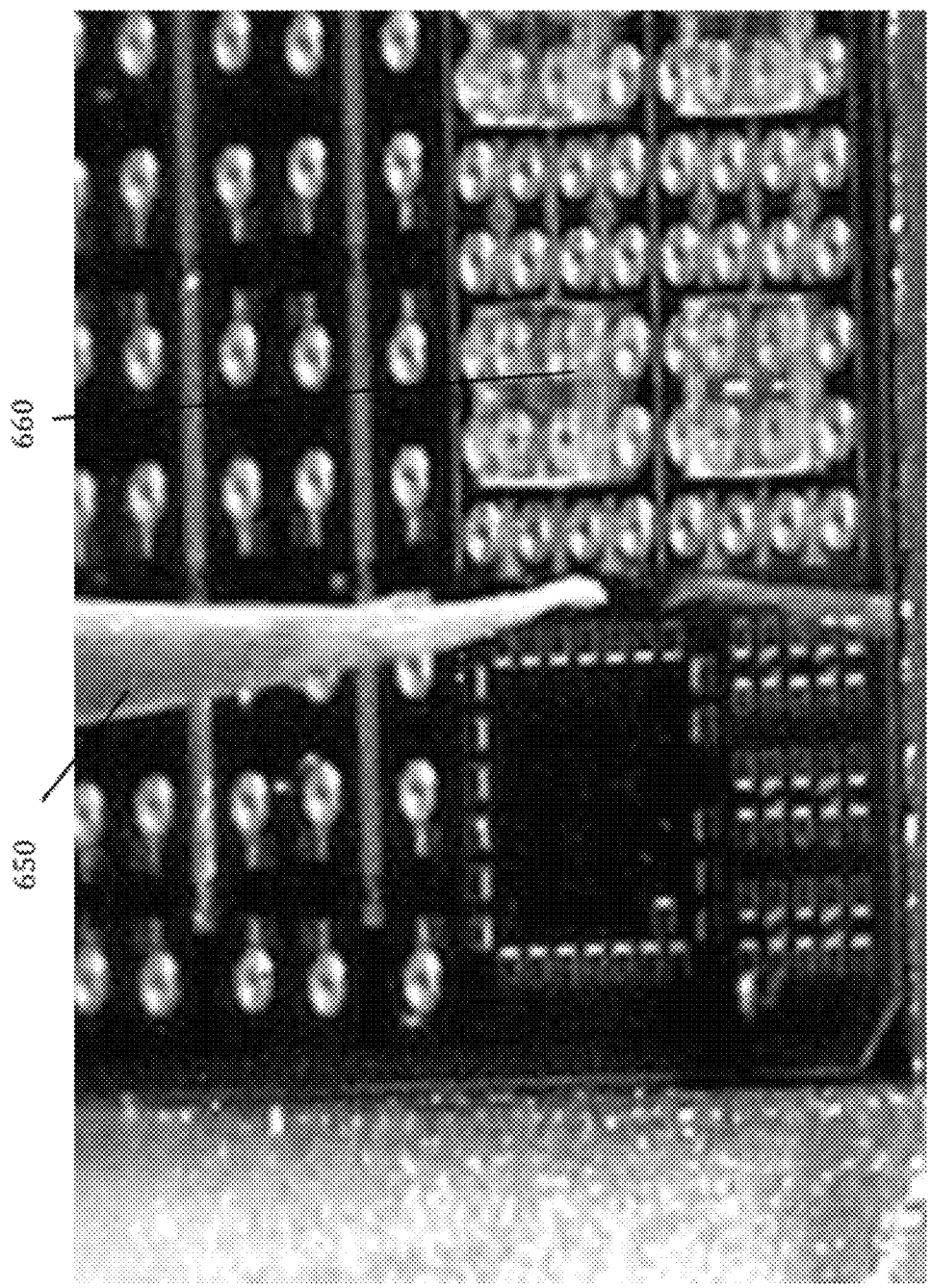
FIG. 7 is a close-up image showing the non-magnetic support and the sensor of FIG. 6 in greater detail.

FIG. 7 is a close-up image showing the non-magnetic support and the sensor of FIG. 6 in greater detail.

Figure 8:
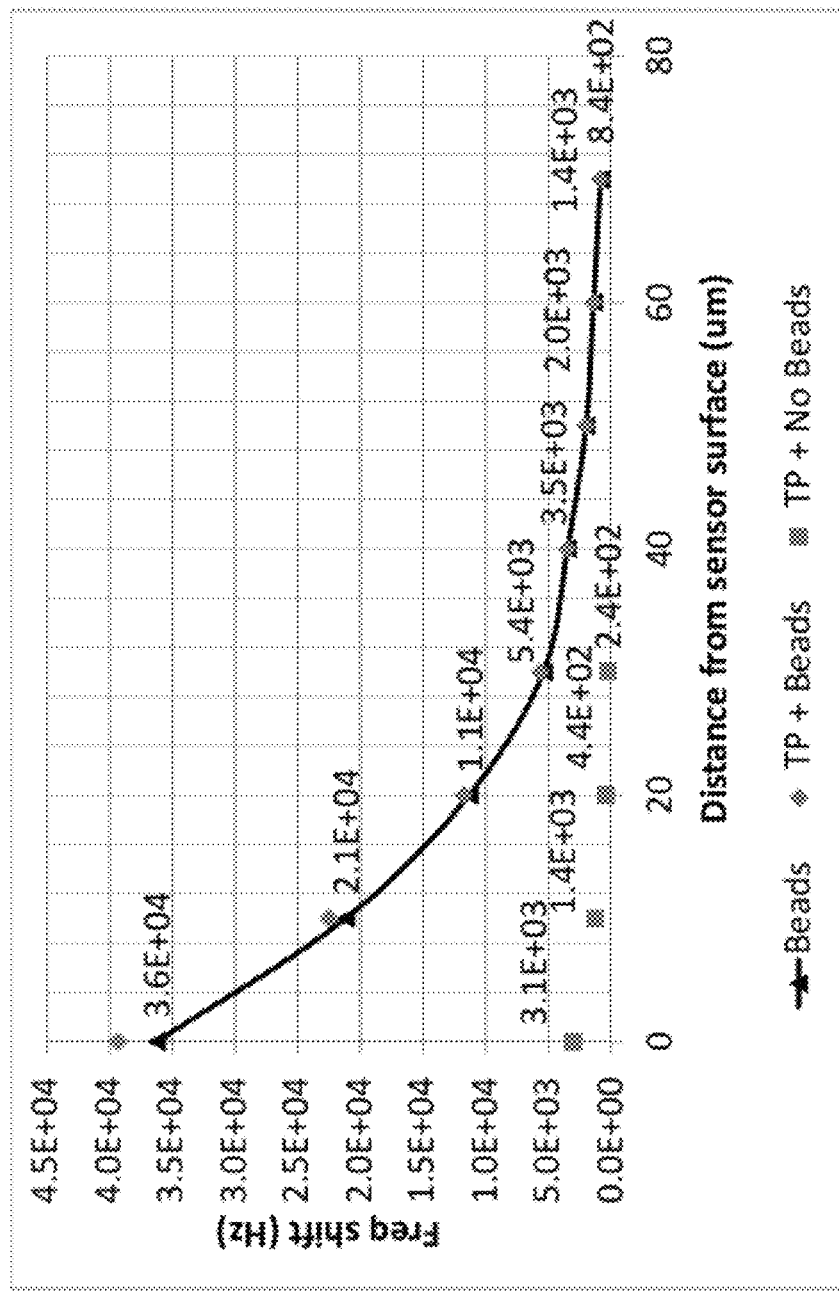
FIG. 8 is a graph showing the frequency shift as a function of height above the sensor (e.g., a vertical sensitivity measurement).

FIG. 8 is a graph showing the frequency shift as a function of height above the sensor (e.g., a vertical sensitivity measurement). In FIG. 8, the vertical axis displays sensor readout, which is the frequency shift of an oscillator in Hertz. The horizontal axis displays distances from the tip of the non-magnetic support having magnetic beads attached to the surface of the sensor, in microns. The line passing through the triangular indicates a calibrated measurement of the sensor response as a function of the distance of the beads from the sensor. This line was determined as a fit to the data obtained by subtracting the signal observed from a bare non-magnetic support (data shown in squares) from the data measured from the non-magnetic support with magnetic beads (data shown in diamonds). It is apparent from the graph that measurements over the range of zero to approximately 70 microns distance between the beads and the sensor surface can be readily observed. The value of the frequency shift for distances approaching zero microns is about 36,000 Hz, while the frequency shift at approximately 70 microns distance is approximately 1400 Hz. Frequency shifts of 840 Hz can be observed as indicated at the extreme right side of FIG. 8.

Figure 9:
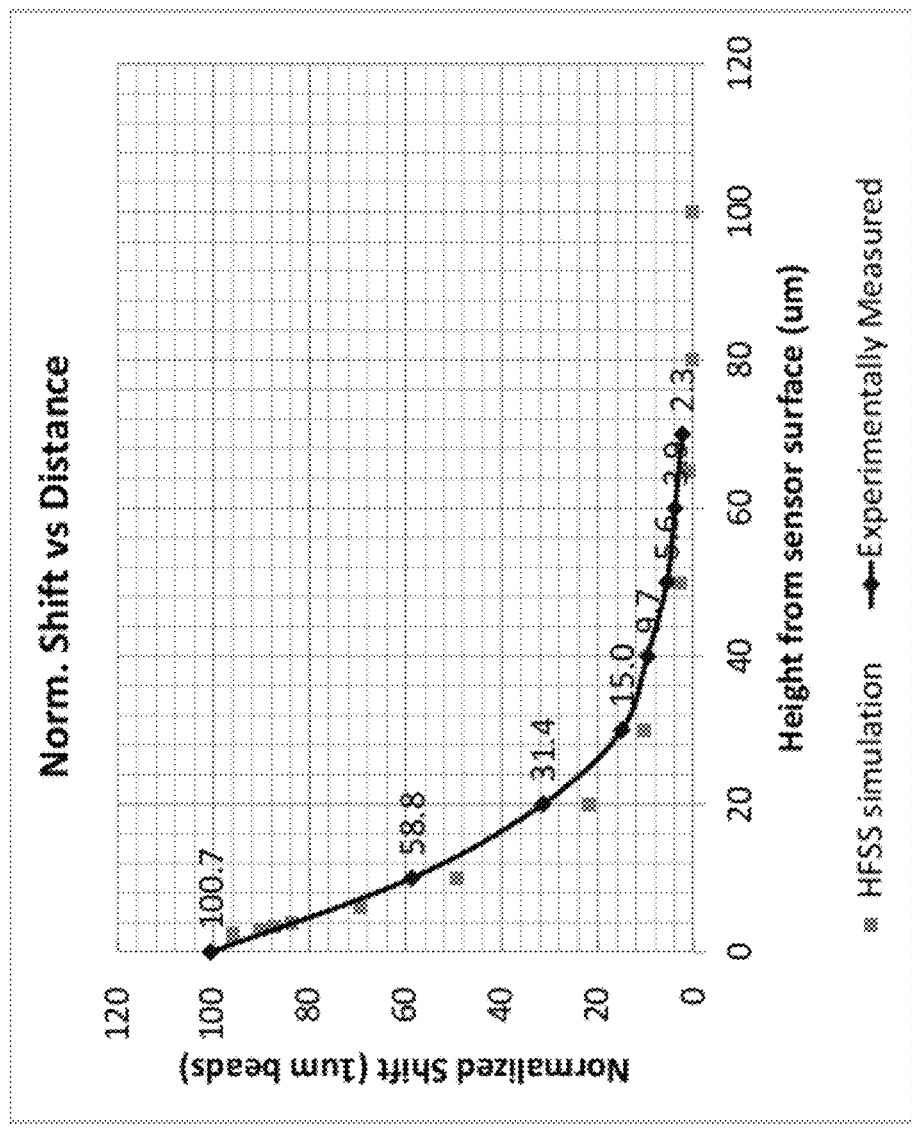
FIG. 9 is a graph showing a comparison of experimental data with simulated results as a function of height above the sensor.

FIG. 9 is a graph showing a comparison of experimental data with simulated results as a function of height above the sensor. The results of vertical sensitivity experiments using 1 micron beads and a non-magnetic support (data indicated by diamonds) are compared to an electromagnetic simulation of 1 micron beads (data indicated by squares) at various distances from the sensor. The electromagnetic simulation was created using the Ansys HFSS simulator. Reasonable but not perfect agreement is observed between the experimental data and the simulation.

Figure 10:
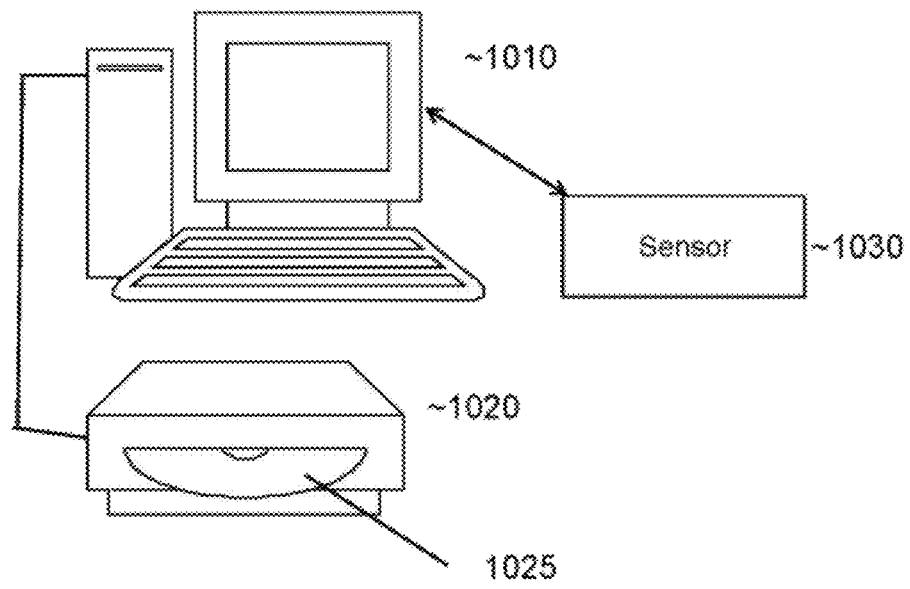
FIG. 10 is a schematic diagram illustrating the relationship between a sensor and a control and analysis module, according to principles of the invention.

FIG. 10 is a schematic diagram illustrating the relationship between a sensor 1030 and a control and analysis module 1010. As illustrated in FIG. 10, the sensor 1030 (or a sensor array 1030) is connected to a control and analysis module 1010 which can be a general purpose programmable computer. The instructions for operating the sensor 1030 and for performing analysis methods according to the invention can be encoded on a machine readable medium 1025 such as a CD-ROM that can be read by a CD-ROM reader/writer 1020 connected to the control and analysis module 1010. The technology to perform the necessary control and analysis functions are well known in the art and commercial embodiments are available.

Binding Moieties

Binding moieties are chosen based on the analyte being detected. Binding moieties include, for example, proteins, including, for example, antibodies, and nucleic acids. In some embodiments, nucleic acids are used to detect other nucleic acids through hybridization. In some embodiments, nucleic acids are aptamers that can bind a variety of analytes or target molecules.

In some embodiments, a detection device can have two or more binding moieties capable of binding the different regions of the same target molecule. In some embodiments, the binding moieties are each nucleic acid molecules that hybridize to different regions of the same target nucleic acid molecule. The binding moieties can be separated by a linker. In one embodiment, the linker allows binding of the two or more binding moieties to the target molecule simultaneously. In some embodiments, the two or more binding moieties are antibodies linked to a linker.

For example, target molecules with multiple binding sites can be used. The multiple binding sites on the target molecules can be composed of the same or different types of binding sites. This increase the chance for the target molecules to interact with the probe molecules and also increase the sensor signal strength per target molecule. Another embodiment can comprise a linker with two binding moieties that are antibodies that are linked to a single linker that connects an electromagnetic detector to electromagnetic material.

In some embodiments, a detection device can have can have two or more binding moieties capable of binding to different target molecules or analytes. Such a device can test for the presence of either of two analytes simultaneously.

Nucleic Acid Binding Moieties

Nucleic acid binding moieties can include a variety of backbone modifications, including, for example, peptide nucleic acids (PNAs), phosphotriesters, methylphosphonates. These nucleic acid analogs are known in the art.

In particular, PNAs are discussed in: Nielsen, "DNA analogues with nonphosphodiester backbones," Annu. Rev. Biophys. Biomol. Struct, 1995; 24:167-83; Nielsen et al., "An introduction to peptide nucleic acid," Curr Issues Mol Biol, 1999; 1(1-2):89-104; and Ray et al., "Peptide nucleic acid (PNA): its medical and biotechnical applications and promise for the future," FASEB J., 2000 June; 14(9): 1041-60; all of which are hereby expressly incorporated by reference in their entirety.

Phophotriesters are discussed in: Sung et al., "Synthesis of the human insulin gene. Part II. Further improvements in the modified phosphotriester method and the synthesis of seventeen deoxyribooligonucleotide fragments constituting human insulin chains B and mini-cDNA," Nucleic Acids Res, 1979 Dec. 20; 7(8):2199-212; van Boom et al., "Synthesis of oligonucleotides with sequences identical with or analogous to the 3'-end of 16S ribosomal RNA of *Escherichia coli*: preparation of m-6-2-A-C-C-U-C-C and A-C-C-U-C-m-4-2C via phosphotriester intermediates," Nucleic Acids Res, 1977 March; 4(3):747-59; and Marcus-Sekura et al., "Comparative inhibition of chloramphenicol acetyltransferase gene expression by antisense oligonucleotide analogues having alkyl phosphotriester, methylphosphonate and phosphorothioate linkages," Nucleic Acids Res, 1987 Jul. 24; 15(14):5749-63; all of which are hereby expressly incorporated by reference in their entirety.

Methylphosphonates are discussed in: U.S. Pat. No. 4,469,863 (Ts'o et al.); Lin et al., "Use of EDTA derivatization to characterize interactions between oligodeoxyribonucleoside methylphosphonates and nucleic acids," Biochemistry, 1989, Feb. 7; 28(3):1054-61; Vyazovkina et al., "Synthesis of specific diastereomers of a DNA methylphosphonate heptamer, d(CpCpApApApCpA), and stability of base pairing with the normal DNA octamer d(TPGPTPTPT-PGPGPC)," Nucleic Acids Res, 1994 Jun. 25; 22(12):2404-9; Le Bec et al., "Stereospecific Grignard-Activated Solid Phase Synthesis of DNA Methylphosphonate Dimers," J Org Chem, 1996 Jan. 26; 61(2):510-513; Vyazovkina et al., "Synthesis of specific diastereomers of a DNA methylphosphonate heptamer, d(CpCpApApApCpA), and stability of base pairing with the normal DNA octamer d(TPGPTPTPT-PGPGPC)," Nucleic Acids Res, 1994 Jun. 25; 22(12):2404-9; Kibler-Herzog et al., "Duplex stabilities of phosphorothioate, methylphosphonate, and RNA analogs of two DNA 14-mers," Nucleic Acids Res, 1991 Jun. 11; 19(11):2979-86; Disney et al., "Targeting a *Pneumocystis carinii* group I intron with methylphosphonate oligonucleotides: backbone charge is not required for binding or reactivity," Biochemistry, 2000 Jun. 13; 39(23):6991-7000; Ferguson et al., "Application of free-energy decomposition to determine the relative stability of R and S oligodeoxyribonucleotide methylphosphonates," Antisense Res Dev, 1991 Fall; 1(3):243-54; Thiviyanathan et al., "Structure of hybrid backbone methylphosphonate DNA heteroduplexes: effect of R and S stereochemistry," Biochemistry, 2002 Jan. 22; 41(3):827-38; Reynolds et al., "Synthesis and thermodynamics of oligonucleotides containing chirally pure R(P) methylphosphonate linkages," Nucleic Acids Res, 1996 Nov. 15; 24(22): 4584-91; Hardwidge et al., "Charge neutralization and DNA bending by the *Escherichia coli* catabolite activator protein," Nucleic Acids Res, 2002 May 1; 30(9):1879-85; and Okonogi et al., "Phosphate backbone neutralization increases duplex DNA flexibility: A model for protein binding," PNAS U.S.A., 2002 Apr. 2; 99(7):4156-60; all of which are hereby incorporated by reference.

Hybridizing Nucleic Acids

Nucleic acids can be used as binding moieties that interact with an analyte or target molecule through hybridization. In some embodiments, the binding moieties comprise a nucleotide sequence of about 10 to 50 bases which is able to specifically bind to a given target sequence to form duplexes by complementary hybridization. In an embodiment, the portion of the binding moiety sequences complementary to the target is comprised between about 10 and about 50 bases, preferably between about 15 and about 40 bases and more preferably between about 20 and about 30 bases. This sequence is considered as the specific sequence for the detection.

In some embodiments, the binding moiety can internally hybridize or can hybridize to another nucleic acid sequence in the detection device (for example, a linker region or another binding moiety). In such embodiments, hybridization of the target molecule will relieve the internal hybridization of the binding moiety. In some embodiments, relief of the internal hybridization will lead to a change in conformation of the detection device. For example, a nucleic acid immobilized on the surface of a detector has two binding moieties. One binding moiety is complementary to a region of the immobilized nucleic acid that also is present on a target molecule. In the absence of a target molecule, the binding moiety can form a loop region in a linker. On binding of a target molecule, binding moieties bind to regions of the target molecule to form a complex. On binding, internal hybridization is relieved and the nucleic acid can achieve an extended conformation of the linker. A force can be applied to the particle. The change in relative distance of the particle from the detector can be detected. In such an embodiment, a complex is energetically more favorable than the internally hybridized structure. The relative free energies of hybridized nucleic acids can be calculated by one of skill in the art, using for example, the relative nucleotide content of sequences to estimate the free energy of binding. Energies also can be experimentally determined, using for example, helix melting temperatures.

Aptamers

A binding moiety can be an aptamer that binds to a desired analyte or analytes. In some embodiments, the aptamer has an average conformation on binding of the analyte that is different from the conformation in the absence of the analyte.

An aptamer will most typically have been obtained by in vitro selection for binding of a target molecule. However, in vivo selection of an aptamer is also possible. Aptamers have specific binding regions which are capable of forming complexes with an intended target molecule in an environment wherein other substances in the same environment are not complexed to the nucleic acid. The specificity of the binding is defined in terms of the comparative dissociation constants (KD) of the aptamer for its ligand as compared to the dissociation constant of the aptamer for other materials in the environment or unrelated molecules in general. A ligand is one which binds to the aptamer with greater affinity than to unrelated material. Typically, the KD for the aptamer with respect to its ligand will be at least about 10-fold less than the KD for the aptamer with unrelated material or accompanying material in the environment. Even more preferably, the KD will be at least about 50-fold less, more preferably at least about 100-fold less, and most preferably at least about 200-fold less. An aptamer will typically be between about 3 and about 300 nucleotides in length. In some embodiments, an aptamer will be between about 5 to 100 nucleotides in length.

Aptamers are known that bind to a variety of molecules. Such aptamers can be used. For example, aptamers are known that bind: isoleucine (Lozupone et al., RNA (2003) Vol. 9, Issue 11, pages 1315-22); Coenzyme A (Saran et al. BMC Evol. Biol. (2003) Vol. 3, Issue 1, pages 26); dopamine (Mannironi et al. Biochemistry (1997) Vol. 36, Issue 32, pages 9726-34); HIV-1 RRE (Boiziau et al. Journal of biological chemistry (1999) Vol. 274, Issue 18, pages 12730-37); ATP (Vaish et al., Biochemistry (2003) Vol. 42, Issue 29, pages 8842-8851); codeine (Win et al., RNA (2006) Vol. 34, Issue 19, pages 5670-82); FAD (Roychowdhury-Saha et al., Biochemistry (2002) Vol. 41, Issue 8, pages 2492-9); Vascular Endothelial Growth Factor (VEGF165) (Ruckman, et al. J. Biol. Chem. (1998) Vol. 273, Issue 32, pages 20556-67); arginine (Tao et al., Biochemistry (1996) Vol. 35, Issue 7, pages 2229-38); S-adenosyle methionine (Burke et al. Nucleic Acids Research (1997) Vol. 25, Issue 10, pages 2020-4); neuroeptide Y (Mendonsa et al., J. Am. Chem. Soc. (2005) Vol. 127, Issue 26, pages 9382-3); human complement C5 (Biesecker et al, Immunopharmacology (1999) Vol. 42, Issue 1-3, pages 219-30); K Ras-Derived Farnesylated Peptide (Gilbert et al. Bioorg. Med. Chem. (1997) Vol. 5, Issue 6, pages 1115-22); *Escherichia coli* rho factor (Schneider et al, FASEB J. (1993) Vol. 7, Issue 1, pages 201-7); Pepocin (Hirao et al., Journal of Biological Chemistry (2000) Vol. 275, Issue 7, pages 4943-8); Ras-binding domain of Raf-1 (Kimotoa et al., FEBS Lett. (1998) Vol. 441, Issue 2, pages 322-6); cellobiose (Yang et al., PNAS (1998) Vol. 95, Issue 10, pages 5462-7); L-arginine (Geiger et al, Nucleic Acids Research (1996) Vol. 24, Issue 6, pages 2755-8); streptavidin (Tahiri-Alaoui et al., Nucleic Acids Res. (2002) Vol. 30, Issue 10, pages e45); cholic acid (Kato et al., Biochim. Biophys. Acta (2000) Vol. 1493, Issue 1-2, pages 12-8); Cyanocobalamin (Lorsch et al., Biochemistry (1994) Vol. 33, Issue 4, pages 973-82); HIV-1 Tar element (Boiziau et al., Antisense Nucleic Acid Drug Dev. (1997) Vol. 7, Issue 4, pages 369-80; Duconge et al., RNA (1999) Vol. 5, Issue 12, pages 1605-14); Tenascin-C (Hicke et al., J. Biol. Chem. (2001) Vol. 276, Issue 52, pages 48644-54); cocaine (Ulrich et al., Proc. Natl. Acad. Sci. USA (1998) Vol. 95, Issue 24, pages 14051-6); S-Adenosylhomocysteine (Gebhardt, Biochemistry (2000) Vol. 39, Issue 24, pages 7255-65); Isoleucine (Legiewicz et al., J. Biol. Chem. (2005)); Sialyl Lewis (Jeong et al., Biochemical and Biophysical Research Communications (2001) Vol. 281, Issue 1, pages 237-43); CD4 (Kraus et al, J. Immunol. (1998) Vol. 160, Issue 11, pages 5209-12); carcinogenic aromatic amines (Brockstedt et al., Biochem. Biophys. Res. Commun (2004) Vol. 313, Issue 4, pages 1004-8); chitin (Fukusaki et al., Bioorg. Med. Chem. Lett. (2000) Vol. 10, Issue 5, pages 423-5); HCV NS3 protease (Urvil et al., European Journal of Biochemistry (1997) Vol. 248, Issue 1, pages 130-8); streptomycin (Wallace et al., RNA (1998) Vol. 4, Issue 1, pages 112-23); substance P (Eulberg et al., Nucleic Acids Res. (2005) Vol. 33, Issue 4, pages e45); Elongation Factor Tu (Hornung et al., Biochemistry (1998) Vol. 37, Issue, pages 7260-7); camp (Koizumi et al., Biochemistry (2000) Vol. 39, Issue 30, pages 8983-92); Hemagglutinin (Gopinath et al., J Biochem (Tokyo)(2006) Vol. 139, Issue 5, pages 837-46; Misono et al. Anal. Biochem. (2005) Vol. 342, Issue 2, pages 312-7); Raf-1 (Kimoto et al., Eur. J. Biochem. (2002) Vol. 269, Issue 2, pages 697-704); aminoglycoside antibiotics (Wang et al., Biochemistry (1996) Vol. 35, Issue 38, pages 12338-46); Subtilisin (Takeno et al., Journal of Biochemistry (1999) Vol. 125, Issue 6, pages 1115-9); factor VIIa (Thromb. Haemost. (2000) Vol. 84, Issue 5, pages 841-8); thrombin (Liu, et al., Journal of Molecular Recognition (2003) Vol. 16, Issue 1, pages 23-27); 7-methyl-guanosine binding RNA (Haller et al., PNAS (1997) Vol. 94, Issue 16, pages 8521-6); malachite green (Flinders et al., Chembiochem (2004) Vol. 5, Issue 1, pages 62-72); tenascin-C (Daniels, PNAS (2003) Vol. 100, Issue 26, pages 15416-21); Ricin A-chain (Hesselberth et al., Journal of Biological Chemistry (2000) Vol. 275, Issue 7, pages 4937-42).

Aptamers are typically developed to bind particular ligands by employing known in vivo or in vitro (most typically, in vitro) selection techniques known as SELEX (Ellington et al., Nature 346, 818-22 (1990); and Tuerk et al., Science 249, 505-10 (1990)). Methods of making aptamers are also described in, for example, U.S. Pat. No. 5,582,981, PCT Publication No. WO 00/20040, U.S. Pat. No. 5,270,163, Lorsch and Szostak, Biochemistry, 33:973 (1994), Mannironi et al., Biochemistry 36:9726 (1997), Blind, Proc. Nat'l. Acad. Sci. USA 96:3606-3610 (1999), Huizenga and Szostak, Biochemistry, 34:656-665 (1995), PCT Publication Nos. WO 99/54506, WO 99/27133, WO 97/42317 and U.S. Pat. No. 5,756,291.

Generally, in their most basic form, in vitro selection techniques for identifying aptamers involve first preparing a large pool of DNA molecules of the desired length that contain at least some region that is randomized or mutagenized. For instance, a common oligonucleotide pool for aptamer selection might contain a region of 20-100 randomized nucleotides flanked on both ends by an about 15-25 nucleotide long region of defined sequence useful for the binding of PCR primers. The oligonucleotide pool is amplified using standard PCR techniques, although any means that will allow faithful, efficient amplification of selected nucleic acid sequences can be employed. The DNA pool is then in vitro transcribed to produce RNA transcripts. The RNA transcripts may then be subjected to affinity chromatography, although any protocol which will allow selection of nucleic acids based on their ability to bind specifically to another molecule (e.g., a protein or any target molecule) may be used. In the case of affinity chromatography, the transcripts are most typically passed through a column or contacted with magnetic beads or the like on which the target ligand has been immobilized. RNA molecules in the pool which bind to the ligand are retained on the column or bead, while nonbinding sequences are washed away. The RNA molecules which bind the ligand are then reverse transcribed and amplified again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the RNA molecules which are capable of acting as aptamers for the target ligand. Once an aptamer sequence has been successfully identified, the aptamer may be further optimized by performing additional rounds of selection starting from a pool of oligonucleotides comprising the mutagenized aptamer sequence. For use in the present invention, the aptamer is preferably selected for ligand binding in the presence of salt concentrations and temperatures which mimic normal physiological conditions.

Antibodies

In some embodiments, antibodies are used as binding moieties. Antibodies are known to bind to a wide variety of molecules and can be selected to bind to many desired molecules using techniques known to one of skill in the art.

Although methods of making monoclonal and polyclonal antibodies are well known in the art, preferred methods are briefly described herein. Variations of the following methods will be apparent to one of skill in the art.

For preparation of polyclonal antibodies, the first step is immunization of the host animal with the immunogen or target molecule. To increase the immune response of the host animal, the immunogen may be combined with an adjuvant. Suitable adjuvants include alum, dextran, sulfate, large polymeric anions, oil and water emulsions, e.g. Freund's adjuvant, Freund's complete adjuvant, and the like. The immunogen may also be conjugated to synthetic carrier proteins or synthetic antigens. A variety of hosts may be immunized to produce the polyclonal antibodies. Such hosts include without limitation, rabbits, guinea pigs, other rodents such as mice or rats, sheep, goats, primates and the like. The immunogen is administered to the host, usually intradermally, with an initial dosage followed by one or more, usually at least two, additional booster dosages. Following immunization, the blood from the host is collected, followed by separation of the serum from the blood cells. The Ig present in the resultant antiserum may be further fractionated using known methods, such as ammonium salt fractionation, DEAE chromatography, and the like.

As with the preparation of polyclonal antibodies, the first step in preparing monoclonal antibodies specific for a target molecule, is to immunize a suitable host. Suitable hosts include rats, hamsters, mice, monkeys and the like, and are preferably mice. Monoclonal antibodies may be generated using the hybridoma method described by Kohler et al., Nature, 256:495 (1975) or by recombinant DNA methods, such as those described in U.S. Pat. No. 4,816,567.

The immunogen is administered to the host in any convenient manner known in the art. For example, and without limitation, administration may be by subcutaneous injection with adjuvants, nitrocellulose implants comprising the immunogen or intrasplenic injections. Alternatively, lymphocytes may be immunized in vitro. The immunization protocol may be modulated to obtain a desired type of antibody, e.g. IgG or IgM, where such methods are known in the art (Kohler and Milstein, Nature, 256:495 (1975)). Booster immunizations may be made, for example one month after the initial immunization. Animals are bled and analyzed for antibody titer. Boosting may be continued until antibody production plateaus. Following immunization, plasma cells are harvested from the immunized host. Sources of plasma cells include the spleen and lymph nodes, with the spleen being preferred.

The plasma cells are then immortalized by fusion with myeloma cells to produce hybridoma cells. Fusion may be carried out by an electrocell fusion process or by using a suitable fusing agent, such as polyethylene glycol, to form a hybridoma cell (Goding, Monoclonal Antibodies: Principles and Practice, pp. 59-109, Academic Press, 1996). The plasma and myeloma cells are typically fused by combining the cells in a fusion medium usually in a ratio of about 10 plasma cells to 1 myeloma cell, where suitable fusion mediums include a fusion agent, e.g. PEG 1000, and the like. Following fusion, the fused cells will be selected, e.g. by growing on HAT medium.

A variety of myeloma cell lines are available. Preferably, the myeloma cell is HGPRT negative, incapable of producing or secreting its own antibodies, and growth stable. Preferred myeloma cells also fuse efficiently and support stable high-level production of antibody by the selected antibody-producing cells. Among these, preferred myeloma cell lines are murine myeloma lines, such as those derived from MOP-21 and MC.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol. 133: 3001 (1984); Brodeur et al., Monoclonal Antibody Production Techniques and Applications, pp. 51-63, Marcel Dekker, Inc., New York, [1987]). Specific cell lines of interest include, for example, p3U1, SP 2/0 Ag14, P3.times.63Ag8.653 (Dr. Greenberg, V.A. Hospital).

Representative hybridomas according to the subject invention include those hybridomas that secrete one of the following monoclonal antibodies: MW1, MW2, MW7, MW8 and hMW9. Each of these antibodies is described in detail below.

Following hybridoma cell production, culture supernatant from individual hybridomas is screened for reactivity with the target molecule, using standard techniques. Such screening techniques are well known in the art and include radioimmunoassay (MA), enzyme-linked immunosorent assay (ELISA), dot blot immunoassays, Western blots and the like. The binding affinity of the monoclonal antibody may, for example, be determined by the Scatchard analysis (Munson et al., Anal. Biochem., 107:220 (1980)).

After hybridoma cells secreting antibodies with the desired specificity, affinity and/or activity are selected, the cells may be subcloned by limiting dilution procedures and grown by standard methods (Goding, Monoclonal Antibodies: Principles and Practice, pp. 59-103, Academic Press, 1996). Culture media may be for example DMEM or RPMI-1640 medium. Alternatively, hybridomas may be grown in vitro as ascites tumors in an animal.

The desired antibody may be purified from the supernatants or ascites fluid by conventional techniques, e.g. affinity chromatography using a target molecule bound to an insoluble support, protein A sepharose and the like.

Human monoclonal antibodies can be made by the hybridoma method. Human myeloma and mouse-human heteromyeloma cell lines for the production of human monoclonal antibodies have been described, for example, by Kozbor, J. Immunol. 133, 3001 (1984), and Brodeur, et al., Monoclonal Antibody Production Techniques and Applications, pp. 51-63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., Proc. Natl. Acad. Sci. USA 90, 2551-255 (1993); Jakobovits et al., Nature 362, 255-258 (1993).

Mendez et al. (Nature Genetics 15: 146-156 [1997]) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous $J_H$ segment as described above. The Xenomouse II harbors 1,020 kb of human heavy chain locus containing approximately 66 $V_H$ genes, complete $D_H$ and $J_H$ regions and three different constant regions, and also harbors 800 kb of human κ locus containing 32 Vκ genes, Jκ segments and Cκ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Alternatively, phage display technology (McCafferty et al., Nature 348, 552-553 [1990]) can be used to produce human antibodies and antibody fragments in vitro, from immunoglobulin variable (V) domain gene repertoires from unimmunized donors.

Binding fragments or binding mimetics of the subject antibodies may also be prepared. These fragments and mimetics preferably share the binding characteristics of the subject antibodies. "Binding characteristics" when used herein include specificity, affinity, avidity, etc. for a target molecule. In one embodiment antibody fragments, such as Fv and Fab may be prepared by cleavage of the intact protein, e.g. by protease or chemical cleavage. Nucleic acid encoding the antibody fragments or binding mimetics may be identified.

Antibody fragments, such as single chain antibodies or scFvs, may also be produced by recombinant DNA technology where such recombinant antibody fragments retain the binding characteristics of the above antibodies. "Antibody fragments" when used herein refer to a portion of an intact antibody, such as the antigen binding or variable region and may include single-chain antibodies, Fab, Fab', F(ab')$_2$ and Fv fragments, diabodies, linear antibodies, and multispecific antibodies generated from portions of intact antibodies.

Recombinantly produced antibody fragments generally include at least the $V_H$ and $V_L$ domains of the subject antibodies, so as to retain the desired binding characteristics. These recombinantly produced antibody fragments or mimetics may be readily prepared from the antibodies of the present invention using any convenient methodology, such as the methodology disclosed in U.S. Pat. Nos. 5,851,829 and 5,965,371; the disclosures of which are herein incorporated by reference. The antibody fragments or mimetics may also be readily isolated from a human scFvs phage library (Pini et al., Curr. Protein Pept. Sci., 1(2):155-69 (2000)) using a target molecule.

Antibodies can be attached to surfaces, linkers and particles using techniques known to one of skill in the art. For example, antibodies can be linked through sulfhydryl groups on the antibody. In some embodiments, sulfhydryl groups on the antibody are first reacted with crosslinking agents that provide an additional reactive group for attachment to a surface, linker, or particle. Techniques for attachment of antibodies can be found, for example, in: Goding, Monoclonal Antibodies: Principles and Practice, pp. 59-103, Academic Press, (1996); Harlow, E., and Lane, D. (1998) Antibodies: A Laboratory Manual. Cold Springs Harbor Laboratory, Cold Springs Harbor, N.Y.; and Hermanson, Greg. Bioconjugate Techniques. Elsevier (2008).

Attachment of Binding Moieties to the Electromagnetic Detector

In some embodiments, the binding moiety is attached to the electromagnetic detector. The attachment can be through a covalent or non-covalent interaction.

Covalent modification of surfaces is known to one of skill in the art. For example, an electromagnetic detector having a gold surface can be modified using sulfur containing binding moiety. In some embodiments, the electromagnetic detector has a silicon nitride, silicon, or glass surface, and the binding moiety is attached through a silane bond. The electromagnetic detector's surface can be modified with silanol compounds to functionalize the surface with reactive groups that are suitable for conjugation to the binding moiety. In some embodiments, the binding moiety will be DNA that has chemical modifications to its 3' and/or 5' end. Such modifications can include thiol groups, amino groups, and others (Iowa DNA Technologies). Binding moieties with chemical modifications can be conjugated to complimentary groups on the surface of the electromagnetic detector. Further, the magnetic probe can be conjugated to the binding moiety via complementary chemical groups as well.

Many strategies for attachment of nucleic acids and proteins to surfaces can be used, including, for example, those disclosed in Hermanson, Greg Bioconjugate Techniques, Elsevier (2008).

In some embodiments, a binding moiety is linked to a surface that is placed adjacent to or near to an electromagnetic detector. In such embodiments, the electromagnetic detector is not in direct contact with the sample containing fluid. The sample containing fluid, with the binding moietie(s) and electromagnetic materials can be included in a separate vessel. In some embodiments, the binding moieties are immobilized on a surface of a dish, plate, slide or other surface, including for example, in 96-well, 356-well, and 1536-well formats. In other embodiments, the binding moieties are immobilized in a microfluidic system. The electromagnetic detectors can be arranged such that the immobilized binding moieties are in physical proximity to the detectors, but not in fluid contact with the detectors. In such an embodiment, the sensors and electronics necessary can be reused, while the sample binding portion disposed of after use. For example a vessel having a surface to which a linker is attached, is placed on a detector which is not in fluid contact with a solution applied to the vessel.

Linkers

In some embodiments, the binding moiety or moities can be attached to the electromagnetic detector (or a surface or substrate that can be placed on or near to the electromagnetic detector) through a linker. Linkers also can be used to attach a binding moiety to an additional binding moiety. Linkers also can be used to link a binding moiety to an electromagnetic material. In some embodiments, a linker is attached to a surface proximal to the electromagnetic detector as well as to an electromagnetic material. In some embodiments, such a linker is attached to one or more binding moieties.

In some embodiments, a linker can be a nucleic acid. In some embodiments, both the binding moieties and the linker are nucleic acids. In such embodiments, the linker generally will not be complementary to a target molecule and does not bind to such target molecule.

Suitable linkers are known to those of skill in the art, and include those from any suitable class of compounds. Polymers or copolymers of organic acids, aldehydes, alcohols, thiols, amines, and the like, are examples of suitable linkers. For example, polymers or copolymers of hydroxy-, amino-, or di-carboxylic acids, such as glycolic acid, lactic acid, sebacic acid, or sarcosine can be used. Alternatively, one can use polymers or copolymers of saturated or unsaturated hydrocarbons such as ethylene glycol, propylene glycol, saccharides, and the like. Linkers also can be nucleic acids. Preferably, the linker should be of an appropriate length that allows an attached binding moiety to interact freely with molecules in a sample solution.

In one embodiment, a linker is attached to the surface of the electromagnetic detector or electromagnetic material by a suitable functional groups on the linker that react with reactive groups already on the solid support. For example, for a solid support that has hydroxyl groups, one can form siloxane bonds by reacting the hydroxyl groups with trichlorosilyl or trialkoxy groups of a linker. Other suitable linkages, and functional groups that can be reacted to form them, include Schiff base (reaction or amine and aldehyde, with or without subsequent reduction to secondary amine), thioether (reaction of thiol with maleimide or acrylamide), disulfide (activated disulfide with thiol), hydrazone (aldehyde or ketone with hydrazine or hydrazide), semicarbazone (aldehyde or ketone with semicarbazide), oxime (aldehyde or ketone with aminooxyacetyl), thiosemicarbazone (aldehyde or ketone with thiosemicarbazide), and thiazolidine (aldehyde and cystein). The linker can also be attached noncovalently to the solid support. For example, either the support or the linker can be conjugated to a biotin moiety, which will form a strong noncovalent linkage to a conjugation partner that displays avidin. Hydrazine-derivatized linkers are described, for example, in Kirchhoff et al. (2001) J. Combinatorial Chem., 3: 71-77.

It is not intended that the linkers be limited to covalent linkages. Linkers can provide suitable functional groups to form non-covalent, e.g., ionic, interactions between one moiety and another (e.g., a detector or solid support and a binding moiety). For example, a linker bound to a solid support or detector can be biotinylated, while a linker or binding moiety can be coupled with an avidin moiety through a reactive group (or vice-versa).

Linkers can be used in a variety of configurations. For example, a detection device can have a linker separating a binding moiety from the electromagnetic detector. In such an embodiment, the linker is attached to both the electromagnetic detector and the binding moiety. A linker also can be used to separate a plurality of binding moieties. In such an embodiment, the linker can have a linear structure, with multiple binding moieties attached to it, or multiple linkers can be used to separate multiple binding moieties. Linkers also can be used to attach a binding moiety to an electromagnetic material. One of skill in the art will recognize that a detection device can have multiple linkers placed in any of the above configurations.

Electromagnetic Materials

In some embodiments, the detection devices include an electromagnetic material. The material will be selected so that it has electromagnetic properties that can be detected by the electromagnetic detector.

Suitable electromagnetic materials include, for example, magnetic particles, charged particles, particles with a dipole moment, and paramagnetic particles. For example, when the electromagnetic detector is a magnetic detector, the electromagnetic material will generally be a particle that is magnetic. The particle also can have other electromagnetic properties that enable detection by an electromagnetic detector. For example, the elecromagnetic material can have a net charge (either positive or negative) or can have a dipole moment. In such cases, the electromagnetic detector can be used to detect a change of the relative position or orientation of the electromagnetic material relative to the electromagnetic detector. In some embodiments, the electromagnetic material is paramagnetic.

One of skill in the art will recognize that one or more electromagnetic materials can be used. The materials can be used at the terminus of a binding moiety or linker, or can be appended at one or more sites along the length of a binding moiety or linker. For example, where the binding moiety is a nucleic acid, electromagnetic materials can be appended to the backbone of the nucleic acid, at positions selected so as not to interfere with hybridization or other interaction between the nucleic acid and the analyte. Where the binding moiety is a nucleic acid that interacts with an analyte through Watson-Crick base-pairing, electromagnetic materials can be attached, for example, to positions on the backbone or bases that do not significantly perturb the base-pairing interaction.

Suitable magnetic particles include monodisperse superparamagnetic particles disclosed, for example, in U.S. Pat. Nos. 5,512,439 and 4,910,148, as well as SiMAG particles Chemicell GmbH (Berlin, Germany); Iron Oxide Nanocrystals nanoparticles, including those sold by Ocean NanoTech (Springdale, Ark.). Iron particles can be coated with polymer or other coatings, including, for example, polyethylene glycol coatings, or can be functionalized with various reactive groups that enable attachment to a linker or binding moiety.

The particle can be covalently attached to the electromagnetic detector, for example, by attachment to a binding moiety or to a binding moiety that is attached to the electromagnetic detector.

In some embodiments, the electromagnetic material is a chelator. Suitable chelators include metal-binding peptides or proteins. Linkers and binding moieties can be modified to include one or more electromagnetic materials. In one embodiment, a linker or binding moiety has one or more metal-binding peptides, for example, a histidine-rich sequence such as $His_6$. Such a metal-binding peptide can be loaded with metal ions that can be detected by the electromagnetic detector.

In some embodiments, the electromagnetic material is a non-peptide chelator. Any chelator capable of binding a detectable metal ion stably can be used, including, for example, macrocyclic chelators. Macrocyclic chelators include, for example, cyclams, porphyrins, and crown ethers. In some embodiments, the chelator binds a detectable metal ion with an affinity of less than $10^{-4}$ M, less than $10^{-5}$ M, or less than $10^{-6}$ M. Suitable metal ions are magnetic or paramagnetic. In one embodiment, the electromagnetic material is a texaphyrin, including those disclosed in U.S. Pat. Nos. 5,162,509; 5,569,759; 7,449,454; 7,112,671; 6,984,734; 6,638,924; 5,969,111; and 5,837,866.

In some embodiments, the electromagnetic material is a protein that includes one or more metal ions. In one embodiment, the protein is ferritin or a homolog of ferritin.

Analytes

The detection devices can be configured to bind a wide variety of analytes. In some embodiments, the analyte is a: protein, nucleic acid, or small molecule, including, for example, drugs, carbohydrates, lipids, steroids, metabolites, intermediates, cofactors, transition state analogs, ions, metals, nucleic acids, and toxins.

Surface Modification of an Electromagnetic Detector

Prior to surface modification of the electromagnetic detector, the detector will be cleaned by sequential rinses in acetone, ethanol, and distilled water, and finally will be sonicated to remove any debris from its surface. Then, the surface of the electromagnetic detector will be cleaned on a molecular scale by one of two methods: (1) plasma etching with oxygen, set at 3 torr and 100 W for 2.5 minutes, or (2) piranha wash, where the electromagnetic detector is cleansed in a 4:1 mix of sulfuric acid and hydrogen peroxide while heated to 110.degree. C. for 5 minutes.

Following the cleaning, the electromagnetic detector will be functionalized using silane chemistry. The silane is prepared by adding 2% (v/v) triethoxysilyludecanal (TESUD) to a 95%/5% mixture of ethanol and water (Gelest, Inc Product Number SIT1984.0). After the silanol condensation reaction has evolved for 5 minutes, the electromagnetic detector or other substrate is immersed in the solution for 2 hours. The surface is then rinsed repeatedly with ethanol and is baked at 110° C. for 30 minutes. In addition, formation of the silane monolayer can occur through chemical vapor deposition (Hozumi and Shirahata, Surface Science, 2006)

DNA will then be printed directly onto the surface of the electromagnetic detector. The DNA will be chemically modified at both its 3' and 5' ends, making the molecule bifunctional. The 5' end will be functionalized with an amine linker, which can bind covalently to the TESUD-treated surface of the electromagnetic detector through formation of a Schiff base. Subsequent reduction using sodium borohydride stabilizes this bond. The 3' end of the DNA will contain a thiol linker that will be used for covalent attachment to a magnetic particle.

To print the DNA at precise locations on the detector surface, we will use a customized SpotBot3 microarrayer from the Array It Corporation. The customized SpotBot3 includes a vision system that allows the user to teach the robot the locations of specific features of the electromagnetic detector to be printed.

Commercially available functionalized beads will be used for the magnetic particle, such as fluidMAG-amine nanoparticles from Chemicell. These beads will be treated with sulfosuccinimidyl-4-[N-maleimidomethyl]cyclohexane-1- carboxylate (sulfo-SMCC) to change the linker group to a maleimide from an amine. Then, the beads will be attached to the DNA probe strands immobilized on the detector surface through reaction of thiol-labeled DNA with bead-labeled maleimide.

Definitions

Unless otherwise explicitly recited herein, any reference to an electronic signal, a magnetic signal, or an electromagnetic signal (or their equivalents) is to be understood as referring to a non-volatile electronic signal, a non-volatile magnetic signal, or a non-volatile electromagnetic signal.

The term "antibody protein" is used herein to refer to a capture agent that has at least an epitope binding domain of an antibody. These terms are well understood by those in the field, and refer to a protein containing one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions. Types of antibodies, including antibody isotypes, monoclonal antibodies and antigen-binding fragments thereof (e.g., Fab, Fv, scFv, and Fd fragments, chimeric antibodies, humanized antibodies, single-chain antibodies, etc) are known and need not be described in any further detail.

An "aptamer" may be a nucleic acid molecule, such as RNA or DNA that is capable of binding to a specific molecule with high affinity and specificity (Ellington et al., Nature 346, 818-22 (1990); and Tuerk et al., Science 249, 505-10 (1990)). Exemplary ligands that bind to an aptamer include, without limitation, small molecules, such as drugs, metabolites, intermediates, cofactors, transition state analogs, ions, metals, nucleic acids, and toxins. Aptamers may also bind natural and synthetic polymers, including proteins, peptides, nucleic acids, polysaccharides, glycoproteins, hormones, receptors and cell surfaces such as cell walls and cell membranes.

The term "binding moiety" refers to an agent that binds a target molecule or analyte through an interaction that is sufficient to permit the agent to bind and concentrate the target molecule from a homogeneous mixture of different molecules. The binding interaction is typically mediated by an affinity region of the binding moiety. Typical binding moieties include any moiety that can specifically bind to a target molecule. In certain embodiments, a polypeptide, e.g., an antibody protein, may be employed. Binding moieties usually "specifically bind" a target molecule. Accordingly, the term "binding moiety" refers to a molecule or a multi-molecular complex which can specifically bind a target molecule, e.g., a phosphorylated polypeptide, with a dissociation constant (KD) of less than about $10^{-6}$ M (e.g., less than about $10^{-7}$ M, less than about $10^{-8}$ M, less than about $10^{-9}$ M, less than about $10^{-10}$ M, less than about $10^{-11}$ M, less than about $10^{-12}$ M, to up to about $10^{-16}$ M) without significantly binding to other molecules. The term "specific binding" refers to the ability of a capture agent to preferentially bind to a particular target molecule that is present in a homogeneous mixture of different target molecule. In certain embodiments, a specific binding interaction will discriminate between desirable and undesirable target molecules in a sample, typically more than about 10 to 100-fold or more (e.g., more than about 1000- or 10.000-fold).

"Complementary" means with respect to a nucleic acid the ability to hybridize to another nucleic acid, including, for example, a target molecule. A nucleic acid generally is complementary based on the interaction of corresponding Watson-Crick base pairs, for example, A-T, A-U, C-G, G-C, U-A and T-A, but also can include interactions between any other nucleotides. Complementary includes a nucleic acid that is entirely Watson-Crick base paired to another nucleic acid, or has one or more mismatched base pairs. In some embodiments, complementary includes nucleic acids that bind under stringent conditions to a target molecule.

"Do/does not bind" as used herein to describe binding moiety-analyte binding, does not mean that there is absolutely no binding at all. Compared to an binding moiety that does bind the analyte, the Ka (association constant for binding between binding moiety and the analyte) for the binding moiety that "does not bind" the aptamer is at least about 10-fold, 100-fold, 1000-fold or more larger than that of the a binding moiety that binds to the analyte, and thus its binding affinity for the analyte is at least about 10-fold, 100-fold, 1000-fold or more weaker than that of the binding moiety that binds to the analyte.

"GMR" or "giant magnetoresistance" means quantum mechanical magnetoresistance effect observed in thin film structures composed of alternating ferromagnetic and non-magnetic layers, which often changes the effective electrical resistance of the thin film in the presence of an external magnetic field.

"Hall effect" means the production of a voltage difference (the Hall voltage) across an electrical conductor, transverse to an electric current in the conductor and a magnetic field perpendicular to the current.

The terms "hybridize" and "hybridization" refer to the formation of complexes between nucleotide sequences which are sufficiently complementary to form complexes via Watson-Crick base pairing.

"Nucleic acid," "nucleic acid sequence," "nucleic acid molecule," and "polynucleotide" refer to a DNA sequence or analog thereof, or an RNA sequence or analog thereof, or combinations thereof, including chimeric molecules. Nucleic acids are formed from nucleotides, including, but not limited to, the nucleotides listed below. A polynucleotide may include analogs of DNA or RNA having modifications to either the bases or the backbone. For example, polynucleotides, as used herein, includes the use of peptide nucleic acids (PNA), phosphorothioates, phosphoramides, phosphorodithioates, O-methylphosphoroamidites, and any other modifications to the backbone.

"Nucleotide" refers to naturally- and non-naturally-occurring nucleotides and nucleotide analogs. Nucleotides include, but are not limited to, adenosine, cytosine, guanosine, thymidine, uracil, 4-acetylcytosine, 8-hydroxy-N-6-methyladenosine, aziridinyl-cytosine, pseudoisocytosine, 5-(carboxyhydroxlmethyl)uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine and 2,6-diaminopurine.

The term "stringent conditions" refers to conditions under which a nucleic acid will hybridize preferentially to, or specifically bind to, its complementary binding partner, and to a lesser extent to, or not at all to, other sequences. Put another way, the term "stringent hybridization conditions" as used herein refers to conditions that are compatible to produce duplexes on an detector surface between complementary binding members, e.g., between a nucleic acid binding moiety and complementary targets in a sample, e.g., nucleic acid probes, such as DNA probes, and their corresponding nucleic acid targets that are present in the sample, e.g., their corresponding mRNA or DNA analytes present in the sample.

Recording the results from an operation or data acquisition, such as for example, recording results at a particular frequency or recording a result corresponding to a change in frequency, is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein, so long as at least some of the implementation is performed in hardware.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, or publication identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A non-optical chemical sensor system, comprising:
   a sensor structure having a surface, said sensor structure configured to measure a distance of a label from said sensor structure surface based on a change in frequency associated with the sensor structure;
   a tether comprising a probe strand of a chemical substance having binding sites disposed along a length of said probe strand, said probe strand having a first end attached to said surface of said sensor structure and having a second end;
   a control and analysis module connected to said sensor structure, said control and analysis module configured to control a non-optical measurement signal applied to said sensor structure and to analyze a measurement signal generated by said sensor structure; and
   said label, wherein said tether is configured to tether said label to said sensor structure surface in the presence of a target chemical compound, and wherein said sensor structure is configured to non-optically sense said label;
   wherein said control and analysis module is programmed to provide a measurement result indicative of the presence of said target chemical compound, said measurement result based on a first measurement of a distance of said label from said surface of said sensor in the absence of said target chemical compound and a second measurement of said distance of said label from said surface of said sensor in the presence of said target chemical compound.

2. The non-optical chemical sensor system of claim 1, wherein said label is connected to said second end of said tether.

3. The non-optical chemical sensor system of claim 1, wherein said non-optical measurement signal is an electrical signal.

4. The non-optical chemical sensor system of claim 1, wherein said label is configured to be subjected to a deliberately applied force.

5. The non-optical chemical sensor system of claim 1, wherein said probe strand comprises a ribonucleic acid.

6. The non-optical chemical sensor system of claim 1, wherein said probe strand comprises a polymer.

7. The non-optical chemical sensor system of claim 1, wherein said sensor structure comprises an LC oscillator, and wherein said frequency is a resonant frequency of said LC oscillator.

8. The non-optical chemical sensor system of claim 1, wherein said tether is configured such that said label is untethered from said sensor structure surface in the absence of said target chemical compound.

9. A non-optical method of performing a chemical assay, comprising:
   providing the non-optical chemical sensor system of claim 1;
   making said first measurement of said distance of said label from said surface of said sensor based on the change in frequency associated with the sensor structure in the absence of a specimen of interest;
   applying a fluid comprising said target chemical compound to be identified to said non-optical chemical sensor system;
   making said second measurement of said distance of said label from said surface of said sensor based on a said change in frequency associated with the sensor structure in the presence of said specimen of interest;
   providing a measurement result indicative of the presence of said target chemical compound in said specimen of interest, said measurement result based on said first measurement and said second measurement; and
   performing at least one of recording said result, transmitting said result to a data handling system, or displaying said result to a user.

10. The non-optical method of performing the chemical assay of claim 9, wherein said label is connected to said second end of said tether.

11. The non-optical method of performing the chemical assay of claim 9, wherein said non-optical measurement signal is a magnetic signal.

12. The non-optical method of performing the chemical assay of claim 9, wherein said non-optical measurement signal is an electrical signal.

13. The non-optical method of performing the chemical assay of claim 9, wherein the sensor structure comprises an LC oscillator.

14. The non-optical method of performing the chemical assay of claim 9, wherein said label is configured to be subjected to a deliberately applied force.

15. The non-optical method of performing the chemical assay of claim 9, wherein said probe strand comprises a ribonucleic acid.

16. The non-optical method of performing the chemical assay of claim 9, wherein said probe strand comprises a polymer.

17. The non-optical chemical sensor system of claim 1, wherein said sensor structure comprises an LC oscillator, and wherein said frequency is a resonant frequency of said LC oscillator.

18. A non-optical chemical sensor system, comprising:
   a sensor structure having a surface, said sensor structure configured to measure a distance of a label from said sensor structure surface based on a change in frequency associated with the sensor structure;
   a tether comprising a probe strand of a chemical substance having binding sites disposed along a length of said probe strand, said probe strand having a first end attached to said surface of said sensor structure and having a second end;
   a control and analysis module connected to said sensor structure, said control and analysis module configured to control a non-optical measurement signal applied to said sensor structure and to analyze a measurement signal generated by said sensor structure; and
   said label, wherein said tether is configured to tether said label to said sensor structure surface in the presence of a target chemical compound, wherein said tether is configured to tether said label to said sensor structure surface in the absence of said target chemical compound, and wherein said sensor structure is configured to non-optically sense said label, wherein said control and analysis module is configured to provide a measurement result indicative of the presence of said target chemical compound, said measurement result based on a first measurement of a distance of said label from said surface of said sensor in the absence of said target chemical compound and a second measurement of said distance of said label from said surface of said sensor in the presence of said target chemical compound.

19. The non-optical chemical sensor system of claim 18, wherein said non-optical measurement signal is a magnetic signal.

* * * * *